United States Patent
Kaneko et al.

(10) Patent No.: US 10,734,103 B2
(45) Date of Patent: Aug. 4, 2020

(54) STRESS MANAGEMENT SYSTEM AND STRESS MANAGEMENT METHOD

(71) Applicant: Panasonic Intellectual Property Management Co., Ltd., Osaka (JP)

(72) Inventors: Yuumi Kaneko, Kanagawa (JP); Atsushi Saso, Kanagawa (JP); Naomi Tomiyama, Kyoto (JP); Takamichi Matsusako, Tokyo (JP); Mikiko Matsuo, Nara (JP); Yuichi Aoki, Osaka (JP); Motoji Ohmori, Osaka (JP)

(73) Assignee: PANASONIC INTELLECTUAL PROPERTY MANAGEMENT CO., LTD., Osaka (JP)

( * ) Notice: Subject to any disclaimer, the term of this patent is extended or adjusted under 35 U.S.C. 154(b) by 0 days.

(21) Appl. No.: 15/681,899

(22) Filed: Aug. 21, 2017

(65) Prior Publication Data
US 2018/0060536 A1 Mar. 1, 2018

(30) Foreign Application Priority Data
Aug. 29, 2016 (JP) .................................. 2016-166856

(51) Int. Cl.
*G16H 15/00* (2018.01)
*G16H 40/63* (2018.01)
(Continued)

(52) U.S. Cl.
CPC ............. *G16H 15/00* (2018.01); *A61B 5/024* (2013.01); *A61B 5/165* (2013.01); *G16H 20/70* (2018.01);
(Continued)

(58) Field of Classification Search
CPC ........ G16H 15/00; G16H 50/70; G16H 50/20; G16H 40/63; G16H 20/70; A61B 5/024; A61B 5/165; A61B 5/167; A61B 5/486
(Continued)

(56) References Cited

U.S. PATENT DOCUMENTS 5,722,418 A * 3/1998 Bro ...................... G06F 19/3456
600/545
7,360,151 B1 * 4/2008 Froloff .................. G06F 40/186
715/255
(Continued)

FOREIGN PATENT DOCUMENTS

JP 2001-344352 12/2001
JP 2012-249797 12/2012
(Continued)

*Primary Examiner* — Carl H Layno
*Assistant Examiner* — Michael J Lau
(74) *Attorney, Agent, or Firm* — Greenblum & Bernstein, P.L.C.

(57) ABSTRACT

There is provided a stress management system that manages psychological stress of a user. The system includes: a first sensor that detects biological data of a user; a second sensor that detects life log data indicating an activity history of the user; a generator that generates stress data using the biological data, the stress data indicating a time series variation in a stress level of the user; an estimator that, when the stress level included in the stress data exceeds a threshold value, estimates whether or not stress experienced by the user is interpersonal stress that is caused by contact with other people, using the life log data; and a notifier that notifies the user of a result of the estimation by the estimator.

19 Claims, 14 Drawing Sheets

(51) Int. Cl.
*G16H 50/20* (2018.01)
*G16H 20/70* (2018.01)
*A61B 5/024* (2006.01)
*G16H 50/70* (2018.01)
*A61B 5/16* (2006.01)
*A61B 5/00* (2006.01)

(52) U.S. Cl.
CPC ............ *G16H 40/63* (2018.01); *G16H 50/20* (2018.01); *G16H 50/70* (2018.01); *A61B 5/167* (2013.01); *A61B 5/486* (2013.01)

(58) Field of Classification Search
USPC ........................................................ 600/300
See application file for complete search history.

(56) References Cited

U.S. PATENT DOCUMENTS

| | | | | |
|---|---|---|---|---|
| 9,189,596 | B2* | 11/2015 | Chen | A61B 5/16 |
| 9,721,450 | B2* | 8/2017 | Kumar | G08B 21/0407 |
| 2001/0049471 | A1* | 12/2001 | Suzuki | A61B 5/0002 |
| | | | | 600/300 |
| 2003/0229497 | A1* | 12/2003 | Wilson | G09B 5/04 |
| | | | | 704/270.1 |
| 2004/0249629 | A1* | 12/2004 | Webster | G10L 13/10 |
| | | | | 704/4 |
| 2005/0154264 | A1* | 7/2005 | Lecompte | A61B 5/486 |
| | | | | 600/300 |
| 2006/0028556 | A1* | 2/2006 | Bunn | G10L 15/25 |
| | | | | 348/211.99 |
| 2006/0095251 | A1* | 5/2006 | Shaw | G10L 15/08 |
| | | | | 704/9 |
| 2009/0043860 | A1* | 2/2009 | Aoki | G06Q 10/107 |
| | | | | 709/206 |
| 2009/0264711 | A1* | 10/2009 | Schuler | A61B 5/16 |
| | | | | 600/300 |
| 2009/0306979 | A1* | 12/2009 | Jaiswal | G10L 15/063 |
| | | | | 704/235 |
| 2010/0318903 | A1* | 12/2010 | Ferren | G06F 40/242 |
| | | | | 715/259 |
| 2012/0151047 | A1* | 6/2012 | Hodges | G06F 21/604 |
| | | | | 709/224 |
| 2014/0101296 | A1* | 4/2014 | Li | H04L 41/0813 |
| | | | | 709/221 |
| 2014/0169547 | A1* | 6/2014 | Murgai | H04M 3/2218 |
| | | | | 379/265.03 |
| 2014/0329214 | A1* | 11/2014 | Bitoun | A61B 5/02055 |
| | | | | 434/262 |
| 2014/0335490 | A1* | 11/2014 | Baarman | A61B 5/002 |
| | | | | 434/236 |
| 2015/0066921 | A1* | 3/2015 | Freimuth | G06F 40/274 |
| | | | | 707/730 |
| 2015/0140527 | A1* | 5/2015 | Gilad-Barach | A61B 5/165 |
| | | | | 434/236 |
| 2015/0272504 | A1* | 10/2015 | Giancardo | A61B 5/486 |
| | | | | 600/595 |
| 2015/0279357 | A1* | 10/2015 | Paxinos | G10L 15/08 |
| | | | | 704/235 |
| 2015/0342511 | A1* | 12/2015 | Goldberg | G06Q 50/22 |
| | | | | 434/236 |
| 2015/0348162 | A1* | 12/2015 | Morris | G06Q 30/0631 |
| | | | | 705/26.7 |
| 2016/0078771 | A1* | 3/2016 | Zhuang | G10L 15/26 |
| | | | | 434/236 |
| 2016/0112681 | A1* | 4/2016 | Kaestle | A61B 5/0077 |
| | | | | 348/78 |
| 2016/0135735 | A1* | 5/2016 | Bowers | A61B 5/4833 |
| | | | | 704/271 |
| 2016/0144150 | A1* | 5/2016 | Berg | A61B 5/053 |
| | | | | 600/28 |
| 2016/0157776 | A1* | 6/2016 | Mestha | A61B 5/02427 |
| | | | | 600/479 |
| 2016/0196836 | A1* | 7/2016 | Yu | H04M 1/72519 |
| | | | | 704/207 |
| 2016/0196837 | A1* | 7/2016 | Levanon | A61B 5/4803 |
| | | | | 704/270 |

FOREIGN PATENT DOCUMENTS

| | | |
|---|---|---|
| JP | 2016-115057 | 6/2016 |
| JP | 2016-163145 | 9/2016 |

* cited by examiner

| USER ID | DATE | TIME | BIOLOGICAL DATA |
|---|---|---|---|
| A | 2016/8/2 | 10:30 | HEART RATE Ba11, BODY TEMPERATURE Ba12, BLOOD PRESSURE Ba13, SWEAT RATE Ba14 |
| B | 2016/8/2 | 10:31 | HEART RATE Ba21, BODY TEMPERATURE Ba22, BLOOD PRESSURE Ba23, SWEAT RATE Ba24 |
| A | 2016/8/2 | 11:30 | HEART RATE Ba31, BODY TEMPERATURE Ba32, BLOOD PRESSURE Ba33, SWEAT RATE Ba34 |
| B | 2016/8/2 | 11:31 | HEART RATE Ba41, BODY TEMPERATURE Ba42, BLOOD PRESSURE Ba43, SWEAT RATE Ba44 |

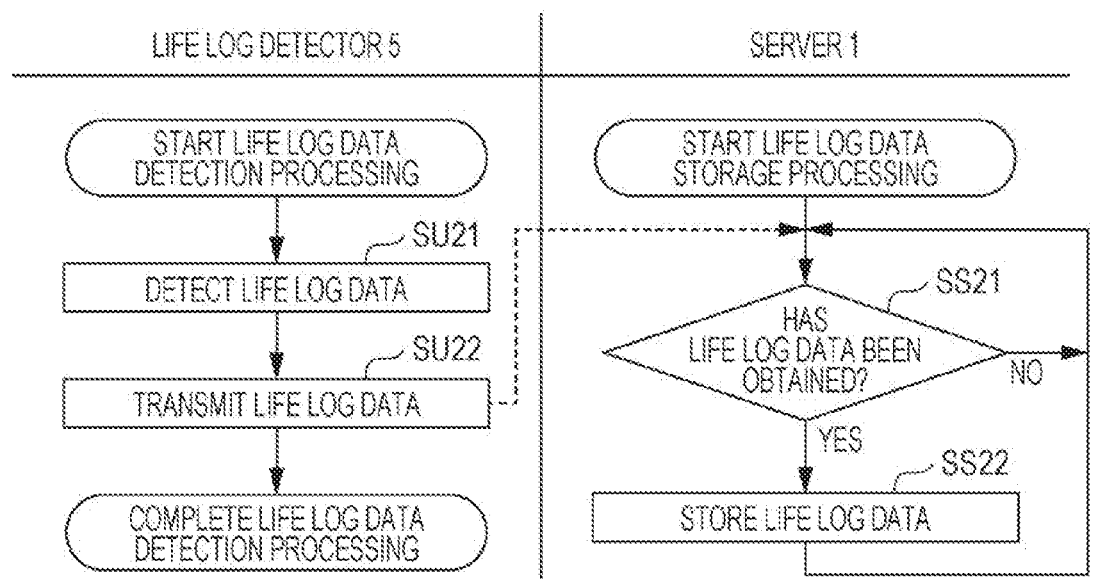

FIG. 9

| TYPE | TERMS |
|---|---|
| POWER HARASSMENT | INCOMPETENT |
| | SALARY THIEF |
| | YOU ARE FIRED |
| | CAN'T YOU DO SUCH A THING? |
| | I WANT TO SEE WHAT YOUR PARENTS ARE LIKE |
| | ... |
| SEXUAL HARASSMENT | WILL YOU HAVE MEALS WITH ME? |
| | WILL YOU PLAY WITH ME? |
| | I LOVE YOU |
| | DON'T DO THAT |
| | I WILL SHOUT |
| | ... |

FIG. 10

| USER ID | SCHEDULE DATA | | |
|---|---|---|---|
| | DATE | HOURS | ACTIVITY |
| A | 2016/8/2 | 10:00 – 12:00 | BUSINESS TRIP |
| A | 2016/8/3 | 13:00 – 15:00 | MEETING |
| B | 2016/8/6 | 13:00 – 16:00 | BASEBALL |
| A | 2016/8/7 | 6:30 – 17:00 | GOLF |
| C | 2016/8/7 | 13:00 – 17:00 | SOCCER |

FIG. 11

| TYPE | ACTIVITY |
|---|---|
| BUSINESS OPERATION | BUSINESS TRIP |
| | MEETING |
| | PAPERWORK |
| | ... |
| SPORTS | GOLF |
| | BASEBALL |
| | SOCCER |
| | ... |
| ... | ... |

FIG. 12

| TYPE | DETAILED TYPE | TECHNICAL TERMS |
|---|---|---|
| BUSINESS OPERATION | NEGOTIATION | DEAL, BREAKOFF, ... |
| | CONTRACT | COMPLIANCE, ... |
| | MEETING | PROGRESS, MEETING MINUTES, AGENDA, ... |
| | ... | ... |
| SPORTS | GOLF | BOGEY, DOUBLE BOGEY, ... |
| | BASEBALL | HIT, HOME RUN, DOUBLE PLAY, ... |
| | SOCCER | GOAL, OFFSIDE, ... |
| | ... | ... |
| ... | ... | ... |

FIG. 13

| TYPE | GENERAL TERMS |
|---|---|
| GOLF | DOUBLE BOGEY |
|  | ... |
| BASEBALL | HANSHIN |
|  | ... |
| SOCCER | GAMBA |
|  | ... |
| ... | ... |

FIG. 15

| USER ID | DATE | STRESS | | STRESS RELIEF METHOD |
| --- | --- | --- | --- | --- |
| | | TYPE | VICTIMIZER | |
| C | 2016/7/1 | POWER HARASSMENT | A | DINING OUT |
| A | 2016/7/3 | GOLF | --- | TAKING BATH |
| A | 2016/7/5 | NEGOTIATION | Z | NEGOTIATION COMPLETED |
| C | 2016/7/7 | SEXUAL HARASSMENT | A | CONSULTING WITH F |
| C | 2016/7/8 | POWER HARASSMENT | B | CONSULTING WITH G |

FIG. 16

| USER ID | PROFILE DATA | | | | | | |
|---|---|---|---|---|---|---|---|
| | NAME | AGE | SEX | INDUSTRY 1 | INDUSTRY 2 | BUSINESS TYPE | POST | HOBBY |
| A | AA | 45 | MALE | MANUFACTURING | ELECTRIC | TECHNICAL | SECTION MANAGER | GOLF, BASEBALL, DRINKING |
| B | BB | 40 | MALE | MANUFACTURING | ELECTRIC | TECHNICAL | ASSISTANT MANAGER | BASEBALL |
| C | CC | 28 | FEMALE | MANUFACTURING | ELECTRIC | SALES | LOWLY EMPLOYEE | SOCCER, DINING OUT |
| D | DD | 25 | FEMALE | MANUFACTURING | ELECTRIC | SALES | LOWLY EMPLOYEE | MOVIE WATCHING, TRAVEL |
| ... | ... | ... | ... | ... | ... | ... | ... | ... |

FIG. 17

| TYPE | STRESS RELIEF METHOD | DATE |
|---|---|---|
| POWER HARASSMENT | CONSULTING WITH SUPERVISOR OF ANOTHER DEPARTMENT | 2016/7/1 |
| SEXUAL HARASSMENT | CONSULTING WITH SUPERVISOR OF ANOTHER DEPARTMENT | 2016/7/3 |
| NEGOTIATION | DINING OUT | 2016/7/5 |
| GOLF | TAKING BATH | 2016/7/7 |
| POWER HARASSMENT | CONSULTING WITH COUNSELLOR | 2016/7/25 |
| SEXUAL HARASSMENT | CONSULTING WITH COUNSELLOR | 2016/7/25 |
| ... | ... | ... |

STRESS MANAGEMENT SYSTEM AND STRESS MANAGEMENT METHOD

BACKGROUND

1. Technical Field

The present disclosure relates to a stress management system and a stress management method that manage psychological stress of a user.

2. Description of the Related Art

In a known conventional technique, a degree (hereinafter called a stress level) of psychological stress experienced by a user is calculated using biological data such as a heart rate and a blood pressure, and psychological stress of the user is managed using the calculated stress level.

For instance, Japanese Unexamined Patent Application Publication No. 2012-249797 discloses that a stress value of a subject is calculated by performing weight addition on a heart rate, a body temperature, a blood pressure, and a sweat rate of the subject using a predetermined coefficient. It is also disclosed that an activity of the subject, a stress value of the subject then, and an image in which the subject conducting the activity is captured are stored in time series in association with each other. It is disclosed that an activity and image of a subject, which are associated with a stress value satisfying a predetermined condition, for instance, a maximum stress value of a day are displayed.

SUMMARY

Further improvement of a stress management system that manages psychological stress of a user is being required.

In one general aspect, the techniques disclosed here feature a stress management system, comprising: a first sensor that detects biological data of a user; a second sensor that detects life log data indicating an activity history of the user; a generator that generates stress data using the biological data, the stress data indicating a time series variation in a stress level of the user; an estimator that, when the stress level included in the stress data exceeds a threshold value, estimates whether or not stress experienced by the user is interpersonal stress that is caused by contact with other people, using the life log data; and a notifier that notifies the user of a result of the estimation by the estimator.

It should be noted that general or specific embodiments may be implemented as an element, a device, an apparatus, a system, an integrated circuit, a method, or any selective combination thereof.

Additional benefits and advantages of the disclosed embodiments will become apparent from the specification and drawings. The benefits and/or advantages may be individually obtained by the various embodiments and features of the specification and drawings, which need not all be provided in order to obtain one or more of such benefits and/or advantages.

BRIEF DESCRIPTION OF THE DRAWINGS

FIG. 5 is a flowchart illustrating the operation of life log data detection processing and life log data storage processing;

FIG. 6 is a table illustrating an example of data stored in a life log storage;

FIG. 9 is a table illustrating an example of an interpersonal stress term table;

FIG. 10 is a table illustrating an example of data stored in a schedule storage;

FIG. 11 is a table illustrating an example of a technical type determination table;

FIG. 12 is a table illustrating an example of a technical term table;

FIG. 13 is a table illustrating an example of a general term table;

FIG. 15 is a table illustrating an example of a specific relief method;

FIG. 16 is a table illustrating an example of data stored in a profile storage;

FIG. 17 is a table illustrating an example of a general relief method table.

DETAILED DESCRIPTION

Figure 1:
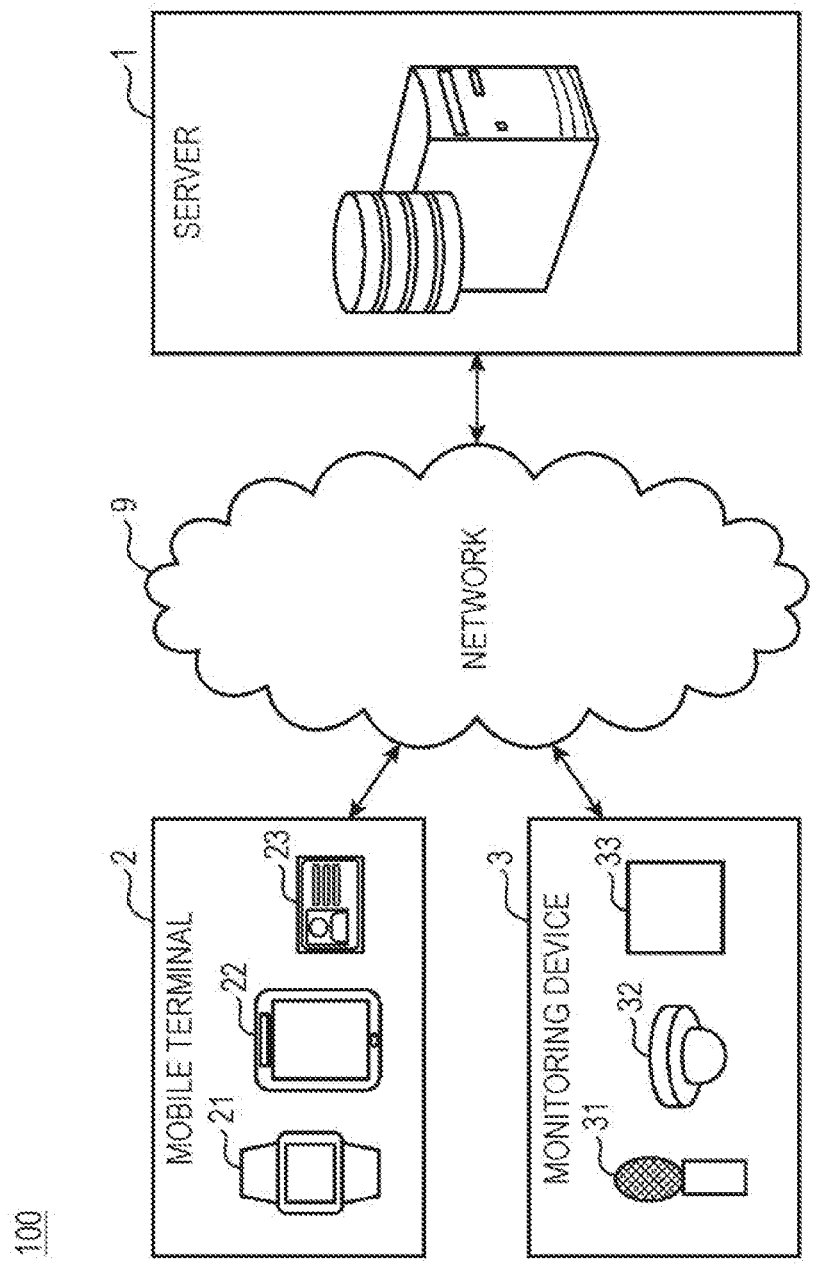
FIG. 1 is a diagram illustrating an overview of a stress management system according to a first embodiment of the present disclosure.

Underlying Knowledge Forming Basis of the Present Disclosure

In recent years, companies have been experiencing a problem of increased number of employees who quit due to interpersonal stress caused by behavior when contacting with other people, such as power harassment, and sexual harassment. Also, schools have been experiencing a problem of increased number of pupils who refuse to attend school due to interpersonal stress, such as bullying, and exclusion from a group.

In recent years, it has been possible to measure biological data using a wearable terminal in a non-contact manner. For this reason, it has become easier than before to detect a stress level of a user from the biological data. In addition, it has become easier to record so-called life log data as image data or voice data using a mobile terminal such as a smartphone, and a camera or a microphone installed in a conference room or a classroom, the life log data indicating an activity history of an employee or a pupil.

Thus, these techniques may be applied to the technique disclosed in Japanese Unexamined Patent Application Publication No. 2012-249797, and the stress level of a user obtained from biological data, and life log data may be stored in association with each other. When a condition is satisfied such that the stress level of a user exceeds a predetermined threshold value, and it is estimated that the user has certain stress, the activity and image of the user may be displayed.

However, in this case, even though the user may find an activity that affects an increase in the stress level, it is not possible for the user to determine whether the stress experienced by the user is caused by emotions such as tension, anxiety of the user at the time of the activity, or is interpersonal stress caused by the activity of contact with other people, such as the utterance or attitude of other people in contact at the time of the activity. For this reason, the user may erroneously determine that the user is experiencing stress caused by emotions of the user although the user is experiencing interpersonal stress. Consequently, the user cannot relieve the interpersonal stress and the above-mentioned problem may not be solved.

Based on the underlying knowledge, the inventors of the present disclosure have intensively studied how to make a user aware of interpersonal stress. As a result, the present disclosure has been completed. Specifically, in the above-described conventional technique, as the first problem, further improvement is necessary in order to make a user aware that the user is experiencing interpersonal stress caused by behavior when contacting with other people. In addition, as the second problem, further improvement is necessary in order to make a user aware of a specific cause of the interpersonal stress.

The present disclosure has been made to cope with the above-mentioned problem, and provides a stress management system and a stress management method capable of making a user aware that the user is experiencing interpersonal stress.

An overview of an aspect of the present disclosure is as follows.

[Item 1]

A stress management system, comprising:

a first sensor that detects biological data of a user;

a second sensor that detects life log data indicating an activity history of the user;

a generator that generates stress data using the biological data, the stress data indicating a time series variation in a stress level of the user;

an estimator that, when the stress level included in the stress data exceeds a threshold value, estimates whether or not stress experienced by the user is interpersonal stress that is caused by contact with other people, using the life log data; and a notifier that notifies the user of a result of the estimation by the estimator.

According to the configuration of Item 1, when the stress level of the user generated using biological data exceeds a predetermined threshold value, whether or not the stress being experienced by the user is interpersonal stress is estimated using, for instance, life log data corresponding to a time of detection of biological data that affects an increase in the stress level. When it is estimated that the stress being experienced by the user is interpersonal stress, the user is notified of a result of the estimation. Thus, it is possible to make the user aware that the user is under interpersonal stress to an extent in which the stress level exceeds a threshold value.

[Item 2]

The stress management system according to Item 1, wherein when the stress experienced by the user is estimated to be interpersonal stress, the estimator further estimates a type of interpersonal stress and a victimizer who is a cause of interpersonal stress using the life log data.

According to the configuration of Item 2, the user is further notified of a result of estimation of the type of interpersonal stress being experienced by the user, and a victimizer who is the cause of the interpersonal stress. Thus, it is possible to further make the user aware that the interpersonal stress being experienced by the user is caused by an activity when contacting with whom and that the interpersonal stress is what type of interpersonal stress. Consequently, the user easily performs an appropriate action for reducing the interpersonal stress being experienced by the user.

[Item 3]

The stress management system according to Item 2, wherein the life log data includes image data in which the user is captured.

According to the configuration of Item 3, image data indicating a situation when the user is performing an activity is included in the life log data used when the estimator makes the estimation. For this reason, the estimator can recognize a person whom the user contacted when conducting an activity, by performing image recognition processing using the image data included in the life log data. Consequently, the estimator can appropriately detect a person with whom the user contacted from a result of the recognition, and can estimate a victimizer who is the cause of interpersonal stress with high accuracy.

[Item 4]

The stress management system according to Item 1, wherein the life log data includes voice data in which a conversation of the user is recorded.

According to the configuration of Item 4, voice data indicating a conversation when the user is performing an activity is included in the life log data used when the estimator makes the estimation. For this reason, the estimator can recognize a person who has had a conversation when the user is performing an activity and the content of the conversation by performing voiceprint recognition processing and voice recognition processing using, for instance, the voice data included in the life log data. Consequently, the estimator can appropriately detect what type of activity the user is performing with whom from a result of the recognition, and can make the estimation with high accuracy.

[Item 5]

The stress management system according to Item 2, further comprising a first storage that stores a first table in which each type of interpersonal stress and a stress relief method for relieving corresponding interpersonal stress are associated with each other, wherein the notifier refers to the first table, and notifies the user of a stress relief method associated with the type of interpersonal stress estimated by the estimator.

According to the configuration of Item 5, the user is notified of a stress relief method for relieving the interpersonal stress being experienced by the user. For this reason, the user can efficiently relieve the interpersonal stress being experienced by the user by conducting an activity in accordance with the notified stress relief method without performing an unnecessary action.

[Item 6]

The stress management system according to Item 5, wherein in the first table, each stress relief method is further associated with product information which indicates usable products when an activity is conducted in accordance with the stress relief method, and the notifier refers to the first table, and notifies the user of the product information associated with the stress relief method which is associated with the type of interpersonal stress estimated by the estimator.

According to the configuration of Item 6, the user is further notified of product information which indicates usable products when an activity is conducted in accordance with the stress relief method. Thus, when the user acts in accordance with the notified stress relief method, the chance for the user to utilize the products indicated by the product information can be increased.

[Item 7]

The stress management system according to Item 2, further comprising:

a first storage that stores, for each user, a first table in which each type of interpersonal stress and a stress relief method for relieving corresponding interpersonal stress are associated with each other; and a second storage that stores a second table in which each user is associated with a profile of corresponding user, wherein the notifier refers to the first table of a first user, and when a stress relief method that is associated with the type of interpersonal stress estimated by the estimator for the first user is not present, the notifier refers to the second table and identifies a second user who has a profile similar to a profile of the first user, then refers to the first table of the second user and notifies the first user of a stress relief method that is associated with the type of interpersonal stress estimated by the estimator for the first user.

The stress relief method for relieving first interpersonal stress of the first user is considered to be substantially the same as the stress relief method for relieving the same type of interpersonal stress as the first interpersonal stress, of the second user having characteristics similar to those of the first user.

In the present aspect, when a stress relief method associated with the type of the first interpersonal stress is not present in the stress relief methods for the first user stored in the first storage, the user is notified of a stress relief method associated with the same type of interpersonal stress as the type of the first interpersonal stress, of the second user having characteristics similar to the characteristics of the first user.

Specifically, according to the configuration of Item 7, the stress relief method of the first and second users having similar characteristics does not need to be stored individually in the first storage as the stress relief method of the first and second users. According to the configuration of item 7, only storing a stress relief method in the first storage as the stress relief method of the first or second user allows the first and second users to be notified of the stress relief method. In this manner, according to the present aspect, it is possible to avoid redundantly storing substantially the same stress relief method in the first storage. Consequently, the storage area of the first storage can be saved.

[Item 8]

The stress management system according to Item 7, further comprising a learner that, when the notifier notifies the first user of the stress relief method then a stress level included in the stress data of the first user falls below the threshold value, estimates a stress relief method that has relieved interpersonal stress, using the life log data of the first user, and stores the estimated stress relief method in the first table in association with the type of interpersonal stress estimated by the estimator for the first user.

According to the configuration of Item 8, when the first user is notified of a stress relief method, then the first interpersonal stress being experienced by the first user is relieved to an extent such that the stress level falls below a threshold value, a method for relieving the first interpersonal stress is estimated. The estimated method is then stored in the first storage as the stress relief method associated with the type of the first interpersonal stress of the first user. Thus, the stress relief method for the first user can be efficiently stored in the first storage without extra effort of the first user.

[Item 9]

The stress management system according to Item 2, further comprising a third storage that stores schedule data indicating an activity schedule of the user, wherein the estimator estimates whether or not stress experienced by the user is interpersonal stress that is caused by contact with other people, using the schedule data.

According to the configuration of Item 9, the estimation is made in consideration of not only an activity history of the user indicated by the life log data, but also an activity schedule of the user indicated by the schedule data. For this reason, the accuracy of the estimation can be improved, as compared with the case where the estimation is made only using the life log data.

[Item 10]

The stress management system according to Item 1, further comprising a terminal that includes both the first sensor and the second sensor.

According to the configuration of Item 10, the stress management system is formed, which is provided with a terminal including both the first sensor and the second sensor. For this reason, the configuration can be simplified, as compared with the case where the stress management system is provided with separate terminals respectively including the first sensor and the second sensor.

In addition, the present disclosure can be implemented not only as a stress management system in a characteristic configuration as described above, but also can be implemented as a stress management method that performs characteristic processing corresponding to the characteristic configuration of the stress management system. Therefore, the same effects as in the above-described stress management system can be provided in another aspect in the following.

[Item 11]

A stress management method, comprising:

detecting biological data of a user;

detecting life log data indicating an activity history of the user;

generating stress data using the biological data, the stress data indicating a time series variation in a stress level of the user;

when the stress level included in the stress data exceeds a threshold value, estimating whether or not stress experienced by the user is interpersonal stress that is caused by contact with other people, using the life log data; and notifying the user of a result of the estimating.

Alternatively, embodiments may be implemented as a computer program that causes a computer to execute characteristic processing included in the stress management method. It goes without saying that such a computer program may be distributed via a non-transitory computer-readable recording medium such as a CD-ROM or a communication network such as the Internet.

It is to be noted that each of the embodiments described below presents a specific example of the present disclosure. The numerical values, shapes, materials, structural components, steps, the sequence of the steps presented in the following embodiments are mere examples, and are not intended to limit the scope of the present disclosure. In addition, among the structural components in the subsequent embodiment, components not recited in any one of the independent claims which indicate the most generic concepts are described as arbitrary structural components. Also, in all embodiments, respective contents may be combined.

First Embodiment

Overview of System

Hereinafter, embodiments of the present disclosure will be described with reference to the drawings. FIG. 1 is a diagram illustrating an overview of a stress management system according to a first embodiment of the present disclosure. As illustrated in FIG. 1, a stress management system 100 includes a mobile terminal 2 carried by a user, a monitoring device 3 installed in a predetermined room such as a conference room or a classroom, a network 9 such as a local area network (LAN) or the Internet, and a server 1.

The mobile terminal 2 includes a wearable terminal 21, a smartphone 22, and an individual identification card 23.

Each of the wearable terminal 21 and smartphone 22 includes a biological sensor, a non-volatile memory, and a wireless communication circuit. The biological sensor detects biological data such as a heart rate, a body temperature, a blood pressure, and a sweat rate of a user. The non-volatile memory stores, for instance, identification information (hereinafter called user ID) of a user.

The wireless communication circuit of the wearable terminal 21 transmits biological data detected by the biological sensor and user ID stored in the non-volatile memory to the smartphone 22 by wireless communication. It is to be noted that the wireless communication circuit of the wearable terminal 21 may transmit biological data and user ID to the server 1 via the network 9 by wireless communication.

The wireless communication circuit of the smartphone 22 transmits the biological data and the user ID, which have been received from the wearable terminal 21, to the server 1 via the network 9 by wireless communication. In addition, the wireless communication circuit of the smartphone 22 transmits biological data detected by itself and user ID stored in the non-volatile memory of itself to the server 1 via the network 9 by wireless communication.

The smartphone 22 further includes a microphone that picks up sound in the surroundings of the smartphone 22, and a camera that captures an image in the surroundings of the smartphone 22. The wireless communication circuit of the smartphone 22 transmits voice data indicating voice picked up by the microphone, image data indicating an image captured by the camera, user ID stored in the non-volatile memory, and the date and hours of picked up voice and captured image to the server 1 via the network 9.

The individual identification card 23 is a so-called IC card in which an integrated circuit (IC) chip is installed. A profile, which is the characteristics of a user, is printed on the surface of the individual identification card 23. The profile of a user includes, for instance, user ID, an image showing the face of the user, a name, and a department. The individual identification card 23 includes a built-in memory chip and wireless communication circuit. The memory chip stores, for instance, data (hereinafter called profile data) indicating the profile of a user. When the individual identification card 23 approaches or comes into contact with a card reader 33, the wireless communication circuit performs wireless communication with the card reader 33. For instance, the wireless communication circuit transmits the profile data stored in the memory chip to the card reader 33 described below. The card reader 33 will be described later.

It is to be noted that the wireless communication circuit of the individual identification card 23 may transmit the profile data stored in the memory chip to the server 1 via the network 9 by wireless communication. Alternatively, the individual identification card 23 may be provided with a biological sensor that detects biological data. Accordingly, the wireless communication circuit of the individual identification card 23 may transmit biological data detected by the biological sensor to the card reader 33 described below. Alternatively, the wireless communication circuit of the individual identification card 23 may transmit biological data detected by the biological sensor to the server 1 via the network 9.

The monitoring device 3 includes, for instance, a sound pick-up microphone 31, a monitoring camera 32, and a card reader 33.

The sound pick-up microphone 31 picks up indoor voice in a room in which the microphone 31 is installed, and transmits voice data indicating picked up voice and the date and hours of the picked up voice to the server 1 via the network 9.

The monitoring camera 32 captures an entire indoor image of the room in which the monitoring camera 32 is installed, and transmits image data indicating the captured image and the date and hours of the captured image to the server 1 via the network 9.

The card reader 33 is installed near the door of a room in which the card reader 33 is installed. When a user enters a room and the individual identification card 23 carried by the user approaches the card reader 33 or the individual identification card 23 comes into contact with the card reader 33, the card reader 33 performs wireless communication with the wireless communication circuit in the individual identification card 23. The card reader 33 obtains profile data stored in the memory chip within the individual identification card 23 by the wireless communication. The card reader 33 then transmits predetermined information included in the obtained profile data, such as user ID to the server 1 via the network 9.

The server 1 receives the data transmitted from the mobile terminal 2 and the monitoring device 3 via the network 9, and performs predetermined processing using the received data. The details of the processing performed by the server 1 will be described later.

Functional Configuration

Figure 2:
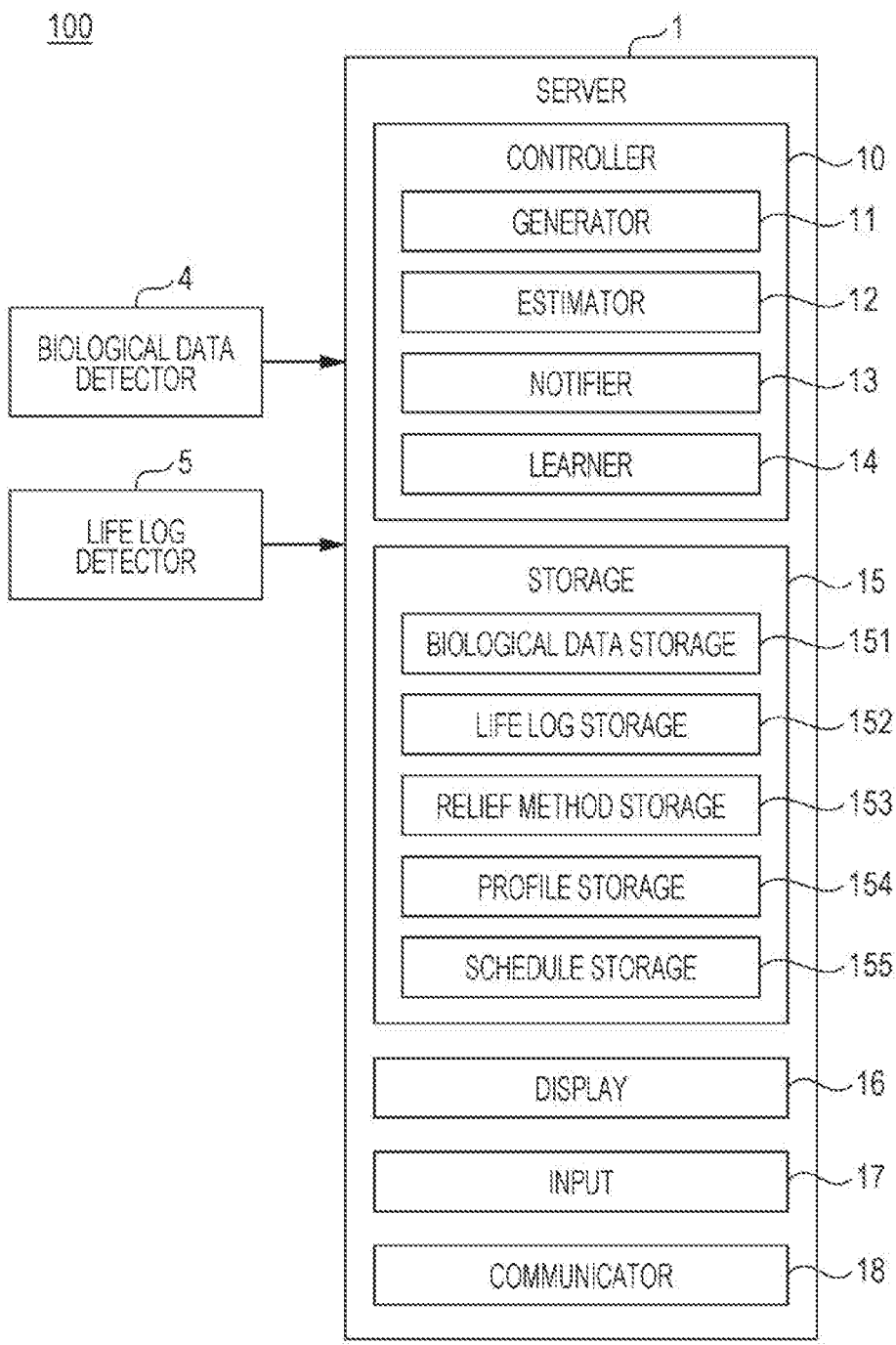
FIG. 2 is a block diagram illustrating an example of a functional configuration of the stress management system according to the first embodiment of the present disclosure.

Next, the functional configuration of the stress management system 100 according to the first embodiment of the present disclosure will be described. FIG. 2 is a block diagram illustrating an example of the functional configuration of the stress management system 100 according to the first embodiment of the present disclosure. The stress management system 100 functions as a biological data detector 4, a life log detector 5, and the server 1. Here, the biological data detector 4 is an example of the first sensor, and the life log detector 5 is an example of the second sensor.

The biological data detector 4 includes the wearable terminal 21 and the smartphone 22 illustrated in FIG. 1. The biological data detector 4 detects biological data of a user by a biological sensor provided in the wearable terminal 21 or the smartphone 22. The biological data detector 4 transmits the detected biological data and the user ID stored in the non-volatile memory of the wearable terminal 21 or the smartphone 22 to the server 1 via the network 9.

The life log detector 5 includes the smartphone 22, the individual identification card 23, and the monitoring device 3 illustrated in FIG. 1. The life log detector 5 detects life log data which indicates the activity history of the user, and transmits the detected life log data, the user ID, and the date and hours of performed activity of the user to the server 1 via the network 9.

Specifically, when a user conducts an activity such as dining out, the life log detector 5 detects voice data and image data as life log data, the voice data indicating a conversation picked up by a microphone provided in the smartphone 22, the image data indicating a situation of the activity captured by a camera provided in the smartphone 22. The life log detector 5 then transmits the life log data, the user ID stored in the non-volatile memory provided in the smartphone 22, and the date and hours of the picked up voice and the captured image to the server 1.

In addition, for instance when a user attends a conference in a room in which the monitoring device 3 is installed, the life log detector 5 detects voice data and image data as life log data, the voice data indicating a conversation picked up by the sound pick-up microphone 31, the image data indicating a situation of the activity captured by the monitoring camera 32. The life log detector 5 then transmits the life log data, the user IDs of all users included in the profile data read by the card reader 33 from the individual identification cards 23 of all users who act in the room, and the date and hours of the picked up voice and the captured image to the server 1.

The server 1 functions as a controller 10, a storage 15, a display 16, an input 17, and a communicator 18.

The controller 10 is formed of a microcomputer including a central processing unit (CPU), a volatile memory such as a random access memory (RAM), and a non-volatile memory such as an electrically erasable programmable read-only memory (EEPROM). The controller 10 controls the operation of each component of the server 1 by causing the CPU to execute a control program stored in the non-volatile memory. The controller 10 functions as a generator 11, an estimator 12, a notifier 13, and a learner 14. The details of the generator 11, the estimator 12, the notifier 13, and the learner 14 will be described later.

The storage 15 includes a storage device such as a hard disk drive (HDD) and a solid state drive (SSD). The storage area owned by the storage 15 is used as a biological data storage 151, a life log storage 152, a relief method storage 153, a profile storage 154, and a schedule storage 155. Here, the relief method storage 153 is an example of the first storage, the profile storage 154 is an example of the second storage, and the schedule storage 155 is an example of the third storage. The details of the biological data storage 151, the life log storage 152, the relief method storage 153, the profile storage 154, and the schedule storage 155 will be described later.

The display 16 is formed of, for instance, a liquid crystal display, and displays a result of processing performed by the controller 10. It is to be noted that the display 16 may be formed of a display device such as a tablet terminal connected to the server 1 to allow communication via the network 9 illustrated in FIG. 1.

The input 17 is provided with a touch panel or a hardware button, for instance, and receives an instruction to the server 1 or input of information from a user.

The communicator 18 is formed of various communication interface circuits for communicating with an external device by the server 1 via the network 9. The external device includes the mobile terminal 2, the monitoring device 3, and an external server (not illustrated) such as a mail server or a web server.

Biological Data Storage Processing

Figures 3, 4:
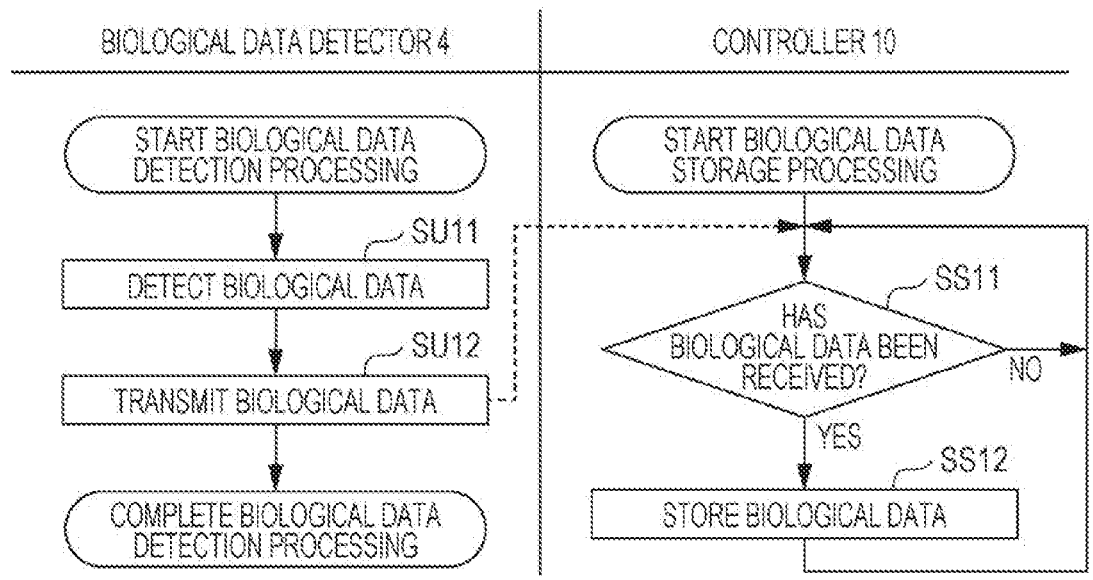
FIG. 3 is a flowchart illustrating the operation of biological data detection processing and biological storage processing.
FIG. 4 is a table illustrating an example of data stored in a biological data storage.

Hereinafter, the operation of the stress management system 100 will be described. The biological data detector 4 performs biological data detection processing to detect biological data of a user regularly, for instance, every hour. In contrast, in the server 1, the controller 10 performs biological data storage processing. The biological data storage processing is processing that stores biological data detected by the biological data detection processing in time series in the biological data storage 151. FIG. 3 is a flowchart illustrating the operation of biological data detection processing and biological storage processing. FIG. 4 is a table illustrating an example of data stored in the biological data storage 151.

Specifically, as illustrated in FIG. 3, when starting the biological data detection processing, the biological data detector 4 detects biological data of a user (SU11). The biological data detector 4 then transmits the biological data detected in SU11 and user ID to the server 1 (SU12). In this embodiment, the biological data detector 4 is assumed to detect a heart rate, a body temperature, a blood pressure, and a sweat rate as biological data. It is to be noted that the biological data detector 4 may detect another item such as a pulse rate as biological data without being limited to those four items.

After the server 1 is started, the controller 10 starts biological data storage processing. Subsequently, the biological data and the user ID transmitted by the biological data detector 4 are received by the communicator 18 (YES in SS11). When the biological data and the user ID are received by the communicator 18, as illustrated in FIG. 4, the controller 10 stores the user ID (for instance, "A"), the date (for instance, "2016/8/2") and the time (for instance, "10:30") on which the biological data and the user ID are received, and the biological data (for instance, "HEART RATE Ba11, BODY TEMPERATURE Ba12, BLOOD PRESSURE Ba13, SWEAT RATE Ba14") in association with each other in the biological data storage 151 (SS12). The controller 10 then returns processing to SS11. Subsequently, the processing in and after SS11 will be performed.

When the biological data and the user ID transmitted by the biological data detector 4 are not received by the communicator 18 (NO in SS11), the controller 10 returns processing to SS11. Subsequently, the processing in and after SS11 will be performed.

Life Log Data Storage Processing

At the timing when an activity of the user is completed, the life log detector 5 performs life log data detection processing to detect life log data of the user. In contrast, in the server 1, the controller 10 performs life log data storage processing. The life log data storage processing is processing that stores the life log data detected by the life log data detection processing in the life log storage 152. FIG. 5 is a flowchart illustrating the operation of the life log data detection processing and the life log data storage processing. FIG. 6 is a table illustrating an example of data stored in the life log storage 152.

Specifically, as illustrated in FIG. 5, when starting the life log data detection processing, the life log detector 5 detects life log data of the user (SU21). In this embodiment, in SU21, the life log detector 5 detects voice data as life log data, the voice data indicating voice when a user conducts an activity. The life log detector 5 then transmits the detected life log data, the user ID, and the date and hours of the picked up voice to the server 1 (SU22).

In contrast, after the server 1 is started, the controller 10 starts the life log data storage processing. Subsequently, the life log data, the user ID, and the date and hours transmitted by the life log detector 5 are received by the communicator 18 (YES in SS21). When the life log data, the user ID, and the date and hours are received by the communicator 18, as illustrated in FIG. 6, the controller 10 stores the user ID, the date and hours, and the life log data in association with each other in the life log storage 152 (SS22). The controller 10 then returns processing to SS21. Subsequently, the processing in and after SS21 will be performed.

For instance, the data in the first row in FIG. 6 indicates the data stored in SS22 when life log data "VOICE DATA A1" detected by a microphone of the smartphone 22 carried by the user identified by the user ID "A", the user ID "A", the date "2016/8/2" and the hours "10:00-12:00" on which voice is picked up by the microphone are transmitted in SU22.

Also, the data in the fourth row in FIG. 6 indicates the data stored in SS22 when life log data ("VOICE DATA A4") detected by the sound pick-up microphone 31, users IDs "C, D" read from the individual identification card 23 carried by the user identified by the user ID "C" and the user identified by the user ID "D", the date "2016/8/2" and the hours "16:00-17:00" on which voice is picked up by the sound pick-up microphone 31 are transmitted in SU22.

Stress Estimation Processing

Figure 7:
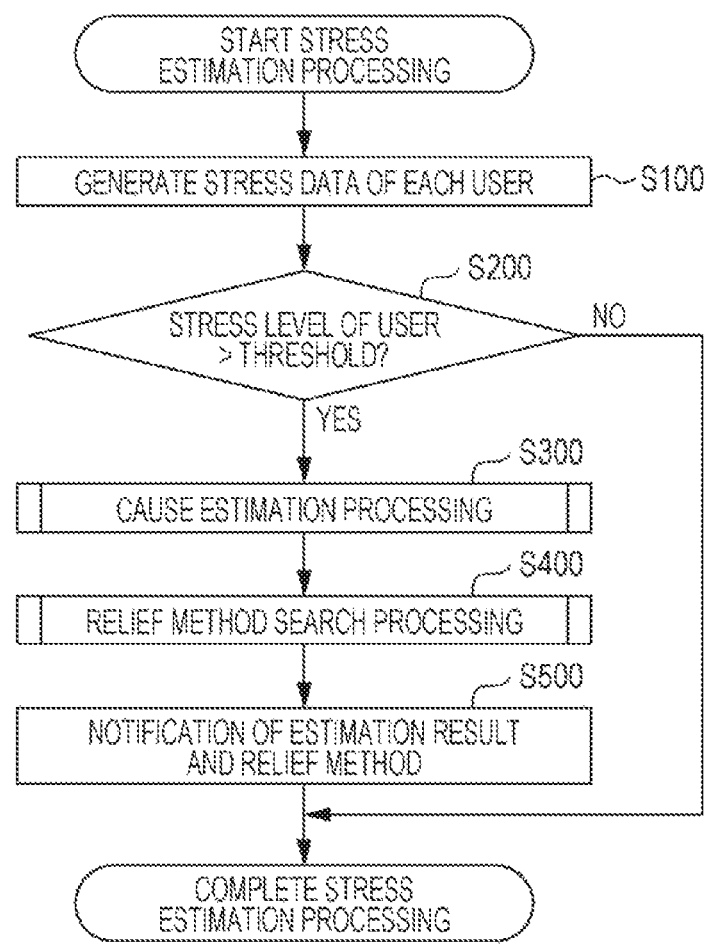
FIG. 7 is a flowchart illustrating the operation of stress estimation processing.

In the server 1, stress estimation processing is performed by the controller 10 at a predetermined timing such as a predetermined time at night (for instance, 0:00 a.m.) or at regular time intervals (for instance, every 2 hours). The stress estimation processing is processing that, when it is determined using biological data that a user is experiencing stress, estimates a type of stress using life log data, and notifies the user of a result of the estimation. Hereinafter, the operation of the stress estimation processing will be described. FIG. 7 is a flowchart illustrating the operation of the stress estimation processing.

As illustrated in FIG. 7, when the stress estimation processing is started, the generator 11 generates stress data which indicates a time series variation in the stress level of each user using the biological data of each user stored in biological data storage 151 (S100).

Hereinafter, S100 will be described in detail. For instance, it is assumed that the data illustrated in FIG. 4 is stored in the biological data storage 151. In this case, in S100, the generator 11 obtains user ID "A" stored in the biological data storage 151.

Next, from the biological data storage 151, the generator 11 refers to one or more pieces of biological data "HEART RATE Ba11, BODY TEMPERATURE Ba12, BLOOD PRESSURE Ba13, SWEAT RATE Ba14", and "HEART RATE Ba31, BODY TEMPERATURE Ba32, BLOOD PRESSURE Ba33, SWEAT RATE Ba34" which are associated with the obtained user ID "A". The order of reference is based on the date and time associated with each piece of biological data which indicates the detection time of the piece of biological data, and biological data is referred to sequentially one by one from the oldest data. Here, biological data is referred to in the order of "2016/8/2 10:30", and "2016/8/2 11:30".

The generator 11 then uses HEART RATE Ba11, BODY TEMPERATURE Ba12, BLOOD PRESSURE Ba13, and SWEAT RATE Ba14 included in the referred piece of biological data "HEART RATE Ba11, . . . " to calculate a stress level at the detection time "2016/8/2 10:30" of the piece of biological data "HEART RATE Ba11, . . . ".

Specifically, the generator 11 calculates the product of the heart rate Ba11 and a first predetermined coefficient, the product of the body temperature Ba12 and a second predetermined coefficient, the product of the blood pressure Ba13 and a third predetermined coefficient, and the product of the sweat rate Ba14 and a fourth predetermined coefficient, then calculates the total of these four products as the stress level. It is to be noted that the calculation method for a stress level using biological data is not limited to this, and may be appropriately changed according to the items detected as the biological data by the biological data detector 4.

In the same manner, the generator 11 uses another piece of biological data "HEART RATE Ba31, . . . " out of the obtained pieces of biological data to calculate a stress level at the detection time "2016/8/2 11:30" of the another piece of biological data "HEART RATE Ba31, . . . ".

The generator 11 then arranges calculated stress levels in order of calculation, and generates arranged data as stress data which indicates a time series variation in the stress level of the user identified by the user ID "A". In the same manner, the generator 11 obtains another user ID stored in the biological data storage 151, and generates stress data which indicates a time series variation in the stress level of the user identified by the obtained another user ID.

FIG. 7 is referred to again. Next, the estimator 12 determines whether or not the stress level included in the stress data of each of the users calculated in S100 exceeds a predetermined threshold value (S200). When it is determined by the estimator 12 that the stress level of a user exceeds a predetermined threshold value (YES in S200), the estimator 12 determines that the user is experiencing stress, and performs cause estimation processing to estimate a cause of the stress regarding the user as a target user (S300).

Specifically, in the cause estimation processing in S300, the estimator 12 estimates a type of stress being experienced by a target user using life log data corresponding to the detection time of biological data that affects an increase in the stress level of the target user. When it is estimated that the stress experienced by the target user is interpersonal stress caused by contact with other people, the estimator 12 further estimates a victimizer who is the cause of the interpersonal stress using the life log data used for the estimation. The details of the cause estimation processing in S300 will be described later.

After S300, the notifier 13 performs relief method search processing (S400). In the relief method search processing of S400, the notifier 13 searches for a stress relief method for relieving the stress of the type estimated in S300. The details of the relief method search processing in S400 will be described later.

After S400, the notifier 13 notifies the target user of a result of the estimation in S300 and the stress relief method retrieved in S400 (S500). For a user, as the target user, whose stress level is determined to exceed a threshold value in S200, S300, S400, and S500 are performed, then the stress estimation processing is completed. Thus, it is possible to make the user aware that interpersonal stress is being experienced by the user to an extent in which the stress level exceeds a threshold value.

Hereinafter, S500 will be described in detail. The storage 15 pre-stores destinations available for the users of the stress management system 100 in association with respective user IDs. Each of the destinations includes a mail address and the IP address of a personal computer used by a user.

In S500, the notifier 13 obtains from the storage 15 a destination associated with the user ID of a target user. The notifier 13 then transmits a message to the obtained destination by the communicator 18, the message including a result of the estimation in S300 and the stress relief method retrieved in S400.

When it is determined in S200 that the stress level of any user does not exceed a threshold value (NO in S200), the estimator 12 completes the stress estimation processing.

Cause Estimation Processing

Figure 8:
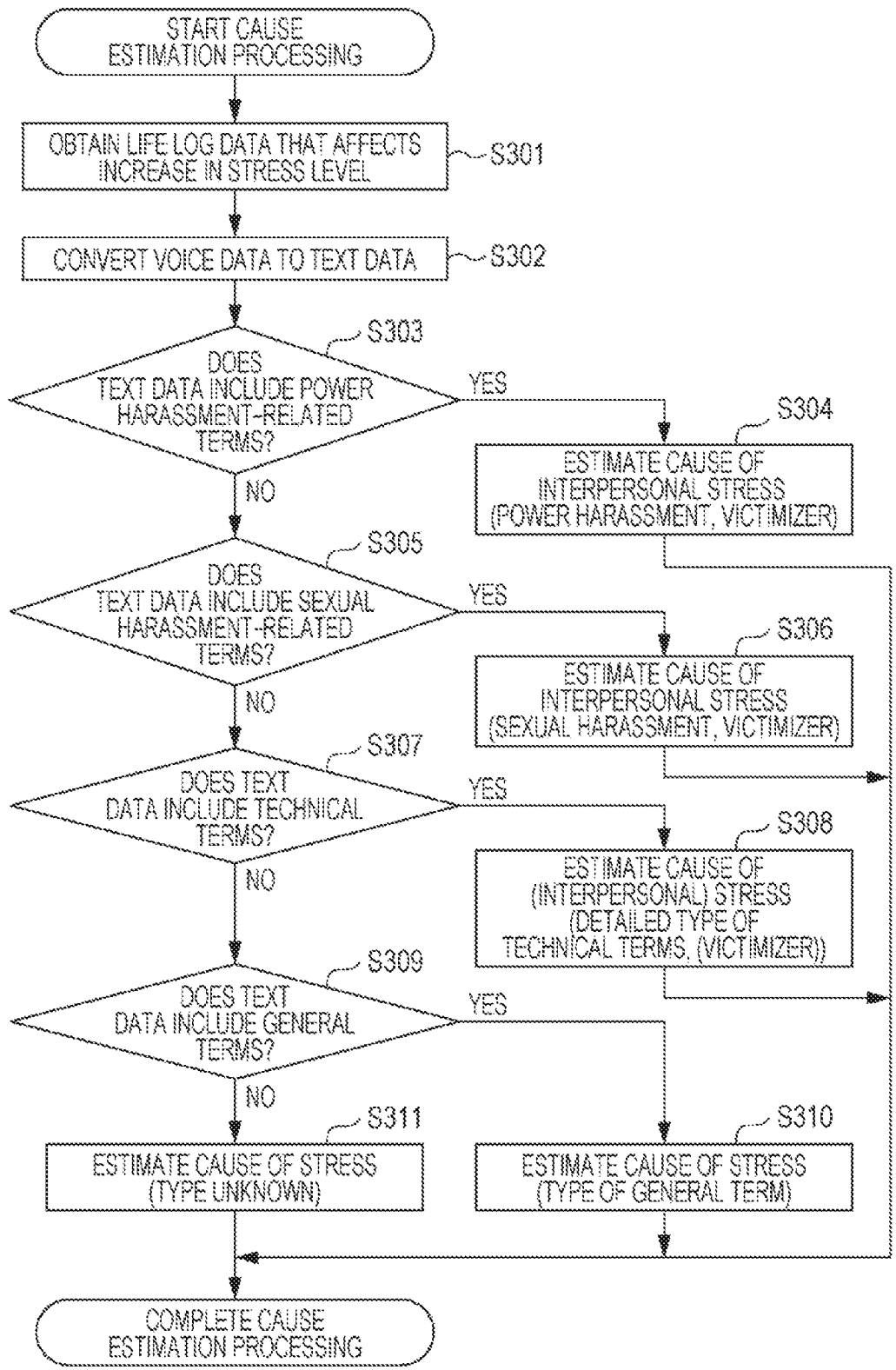
FIG. 8 is a flowchart illustrating the operation of cause estimation processing.

Hereinafter, the cause estimation processing in S300 illustrated in FIG. 7 will be described in detail. FIG. 8 is a flowchart illustrating the operation of the cause estimation processing. As illustrated in FIG. 8, when starting the cause estimation processing, the estimator 12 obtains life log data corresponding to the detection time of biological data that affects an increase in the stress level (S301).

Specifically, in S301, from the biological data storage 151 illustrated in FIG. 4, the estimator 12 obtains a date (for instance, "2016/8/2") and a time (for instance, "10:30") associated with the biological data (for instance, "HEART RATE Ba11, . . . ") used for calculation of the stress level which has been determined to exceed a threshold value in S200. Thus, the estimator 12 recognizes the time point (for instance, "2016/8/2 10:30") indicated by the obtained date and time as the detection time of biological data that affects an increase in the stress level.

Out of the life log data (for instance, "VOICE DATA A1", "VOICE DATA A3") associated with the user ID (for instance, "A") of the target user, the estimator 12 obtains life log data (for instance, "VOICE DATA A1") associated with date and hours (for instance, "2016/8/2", "10:00-12:00") including the recognized detection time (for instance, "2016/8/2 10:30") of biological data in the life log storage 152 illustrated in FIG. 6. Thus, the estimator 12 obtains life log data corresponding to the detection time of biological data that affects an increase in the stress level.

Next, the estimator 12 converts voice data (for instance, "VOICE DATA A1") included in the life log data into text data which indicates the content of a conversation when the target user conducts an activity (S302). Specifically, in S302, the estimator 12 performs publicly known voice recognition processing, and thereby recognizes the voice in a conversation of a person, included in the voice indicated by the voice data included in the life log data obtained in S301, and generates text data which indicates the content of the conversation.

Next, the estimator 12 determines whether or not the text data converted in S302 includes power harassment related terms (S303). When it is determined that the text data converted in S302 includes no power harassment related terms (NO in S303), the estimator 12 determines whether or not the text data includes sexual harassment related terms (S305).

Hereinafter, S303 and S305 will be described in detail. FIG. 9 is a table illustrating an example of an interpersonal stress term table. For instance, as illustrated in FIG. 9, the storage 15 pre-stores an interpersonal stress term table in which a type of interpersonal stress and terms related to each interpersonal stress are associated with each other.

Specifically, in S303, the estimator 12 determines whether or not the text data converted in S302 includes any of the terms (for instance, "INCOMPETENT", "SALARY THIEF") associated with "POWER HARASSMENT" in the interpersonal stress term table illustrated in FIG. 9. In the same manner, in S305, the estimator 12 determines whether or not the text data converted in S302 includes any of the terms (for instance, "WILL YOU HAVE MEALS WITH ME?", "WILL YOU PLAY WITH ME?") associated with "SEXUAL HARASSMENT" as a type of interpersonal stress in the interpersonal stress term table illustrated in FIG. 9.

In S303, when it is determined that the text data converted in S302 includes any of power harassment related terms (YES in S303), the estimator 12 estimates that the target user is experiencing interpersonal stress. In addition, the estimator 12 estimates that the type of the interpersonal stress is "POWER HARASSMENT". In addition, the estimator 12 estimates a victimizer who is the cause of the interpersonal stress using voice data (hereinafter called pre-conversion voice data) before converted to text data in S302 and the text data (S304). The estimator 12 then completes the cause estimation processing, In S305, when it is determined that the text data converted in S302 includes any of sexual harassment related terms (YES in S305), the estimator 12 estimates that the target user is experiencing interpersonal stress. In addition, the estimator 12 estimates that the type of the interpersonal stress is "SEXUAL HARASSMENT". In addition, the estimator 12 estimates a victimizer who is the cause of the interpersonal stress using the pre-conversion voice data and the text data (S306). The estimator 12 then completes the cause estimation processing.

Hereinafter, the estimation method for a victimizer who is the cause interpersonal stress in S304 and S306 will be described in detail. The storage 15 stores the user ID of each user and voice data (hereinafter called user voice data) indicating the voice of the user in association with each other beforehand.

In S303, when it is determined that the text data converted in S302 includes any of power harassment related terms, the estimator 12 extracts voice data associated with the power harassment related terms from the pre-conversion voice data in S304. In the same manner, in S305, when it is determined that the text data converted in S302 includes any of sexual harassment related terms, the estimator 12 extracts voice data associated with the sexual harassment related terms from the pre-conversion voice data in S304.

The estimator 12 performs publicly known voiceprint recognition processing in S304 and S306, thereby identifies user voice data with a voiceprint that matches the voiceprint of the extracted voice data, from the user voice data stored in the storage 15. The estimator 12 then obtains from the storage 15 the user ID associated with the identified user voice data, The estimator 12 estimates that the user identified by the obtained user ID is the victimizer who is the cause of interpersonal stress.

On the other hand, when it is determined that the text data converted in S302 includes no sexual harassment related terms (NO in S305), the estimator 12 determines whether or not the text data converted in S302 includes a technical term (S307).

Hereinafter, S307 will be described in detail. FIG. 10 is a table illustrating an example of data stored in the schedule storage 155. FIG. 11 is a table illustrating an example of a technical type determination table. FIG. 12 is a table illustrating an example of a technical term table.

As illustrated in FIG. 10, the schedule storage 155 illustrated in FIG. 2 stores, via the network 9, the user ID (for instance, "A") of the user and schedule data indicating an activity schedule of the user in association with each other by an application in the smartphone 22 carried by a user or a personal computer (not illustrated) used by a user. The schedule data includes a scheduled date (for instance, "2016/8/2") and hours (for instance, "10:00-12:00") on which a user is going to conduct an activity, and the content (hereinafter called an action content) of a scheduled activity (for instance, "BUSINESS TRIP").

As illustrated in FIG. 11, the storage 15 pre-stores a technical type determination table in which a type of technical term (for instance, "BUSINESS OPERATION"), and terms (for instance, "BUSINESS TRIP", "MEETING", "PAPERWORK") which may be used as activity content included in the schedule data are associated with each other.

As illustrated in FIG. 12, the storage 15 pre-stores a technical term table in which a type (for instance, "BUSINESS OPERATION") of technical term, a detailed type (hereinafter called a detailed type of technical term) of technical term (for instance, "NEGOTIATION"), and technical terms (for instance, "DEAL", "BREAKOFF") are associated with each other.

In S307, the estimator 12 first refers to the schedule data illustrated in FIG. 10, stored in the schedule storage 155, and from schedule data associated with the user ID (for instance, "A") of a target user, obtains schedule data which includes the date (for instance, "2016/8/2") of the recognized detection time (for instance, "2016/8/2 10:30") of biological data obtained in S301, and hours (for instance, "10:00-12:00") including the time (for instance, "10:30") of the detection time. Thus, the estimator 12 obtains schedule data corresponding to the detection time of biological data that affects an increase in the stress level recognized in S301.

The estimator 12 then refers to the technical type determination table illustrated in FIG. 11, and obtains a type (for instance, "BUSINESS OPERATION") of technical term associated with activity content (for instance, "BUSINESS TRIP") included in the obtained schedule data. Thus, the estimator 12 recognizes the obtained type of technical term as a type of technical term which may be included in a conversation when an activity is conducted at the detection time of biological data.

The estimator 12 then refers to the technical term table illustrated in FIG. 12, then refers to technical terms (for instance "DEAL", "BREAKOFF", "COMPLIANCE", "PROGRESS", "MEETING MINUTES", "AGENDA") associated with the obtained type (for instance, "BUSINESS OPERATION") of technical term, and determines whether or not the text data converted in S302 includes any of the associated technical terms.

In S307, when it is determined that the text data converted in S302 includes a technical term (for instance, "BREAKOFF") (YES in S307), the estimator 12 refers to the technical term table illustrated in FIG. 12, and estimates that the detailed type (for instance, "NEGOTIATION") of technical term associated with the technical term (for instance, "BREAKOFF") is the type of stress being experienced by the target user. In addition, the estimator 12 estimates presence or absence of a victimizer who is the cause of the stress by using pre-conversion voice data and the text data (S308). The estimator 12 then completes the cause estimation processing.

Specifically, in S308, similarly to S304 and S306, the estimator 12 extracts from the pre-conversion voice data voice data associated with a technical term which is determined to be included in the text data in S307. The estimator 12 then performs publicly known voiceprint recognition processing, thereby determining whether or not user voice data with a voiceprint matching the voiceprint of the extracted voice data is present in the storage 15. When it is determined that user voice data with a voiceprint matching the voiceprint of the extracted voice data is present, the estimator 12 obtains the user ID associated with the user voice data from the storage 15. The estimator 12 then estimates that the user identified by the obtained user ID is a victimizer who is the cause of stress.

When a victimizer who is the cause of stress is estimated in S308, the estimator 12 estimates that the user is experiencing interpersonal stress. In this case, the estimator 12 estimates that the detailed type (for instance, "NEGOTIATION") of technical term associated with the technical term in the technical term table illustrated in FIG. 12 is the type of the interpersonal stress.

It is to be noted that in S304, S306 and S308, the estimator 12 refers to the data (FIG. 6) stored in the life log storage 152. When multiple user IDs (for instance, "A, B") associated with life log data (for instance, "VOICE DATA A3") obtained in S301 are present, the estimator 12 may obtain user ID (for instance, "B") different from the user ID (for instance, "A") of the target user, out of the multiple user IDs. The estimator 12 may estimate that the user identified by the obtained user ID (for instance, "B") is a victimizer who is the cause of interpersonal stress.

When it is determined that the text data converted in S302 includes no technical term (NO in S308), the estimator 12 determines whether or not the text data converted in S302 includes a general term (S309).

Hereinafter, S309 will be described in detail. FIG. 13 is a table illustrating an example of a general term table. As illustrated in FIG. 13, the storage 15 pre-stores a general term table in which a type (for instance, "GOLF") of general term, and a general term (for instance, "DOUBLE BOGEY") of the type are associated with each other. In S309, the estimator 12 determines whether or not the text data converted in S302 includes one of general terms (for instance, "DOUBLE BOGEY", "HANSHIN", "GAMBA") stored in the general term table illustrated in FIG. 13.

In S309, when it is determined that the text data converted in S302 includes a general term (for instance, "DOUBLE BOGEY") (YES in S309), the estimator 12 estimates that the target user is experiencing stress caused by emotions of the user, and not interpersonal stress. The estimator 12 refers to the general term table illustrated in FIG. 13, and estimates a type (for instance, "GOLF") of general term associated with the general term is the type of stress being experienced by the user (S310). The estimator 12 then completes the cause estimation processing.

On the other hand, when it is determined that the text data converted in S302 includes no general term (NO in S309), the estimator 12 estimates that the target user is experiencing unknown stress (S311). The estimator 12 then completes the cause estimation processing.

In this manner, when it is estimated that the target user is experiencing interpersonal stress in the cause estimation processing, the estimator 12 estimates a type of the interpersonal stress and a victimizer who is the cause of the interpersonal stress using the life log data used for the estimation. Thus, in S500 illustrated in FIG. 7, the target user is notified of a result of the estimation of a type of the interpersonal stress being experienced by the target user and a victimizer who is the cause of the interpersonal stress. Thus, it is possible to further make the target user aware that the interpersonal stress being experienced by the target user is caused by an activity when contacting with whom and that the interpersonal stress is what type of interpersonal stress. Consequently, the target user easily performs an appropriate action for reducing the interpersonal stress being experienced by the target user.

Relief Method Search Processing

Figure 14:
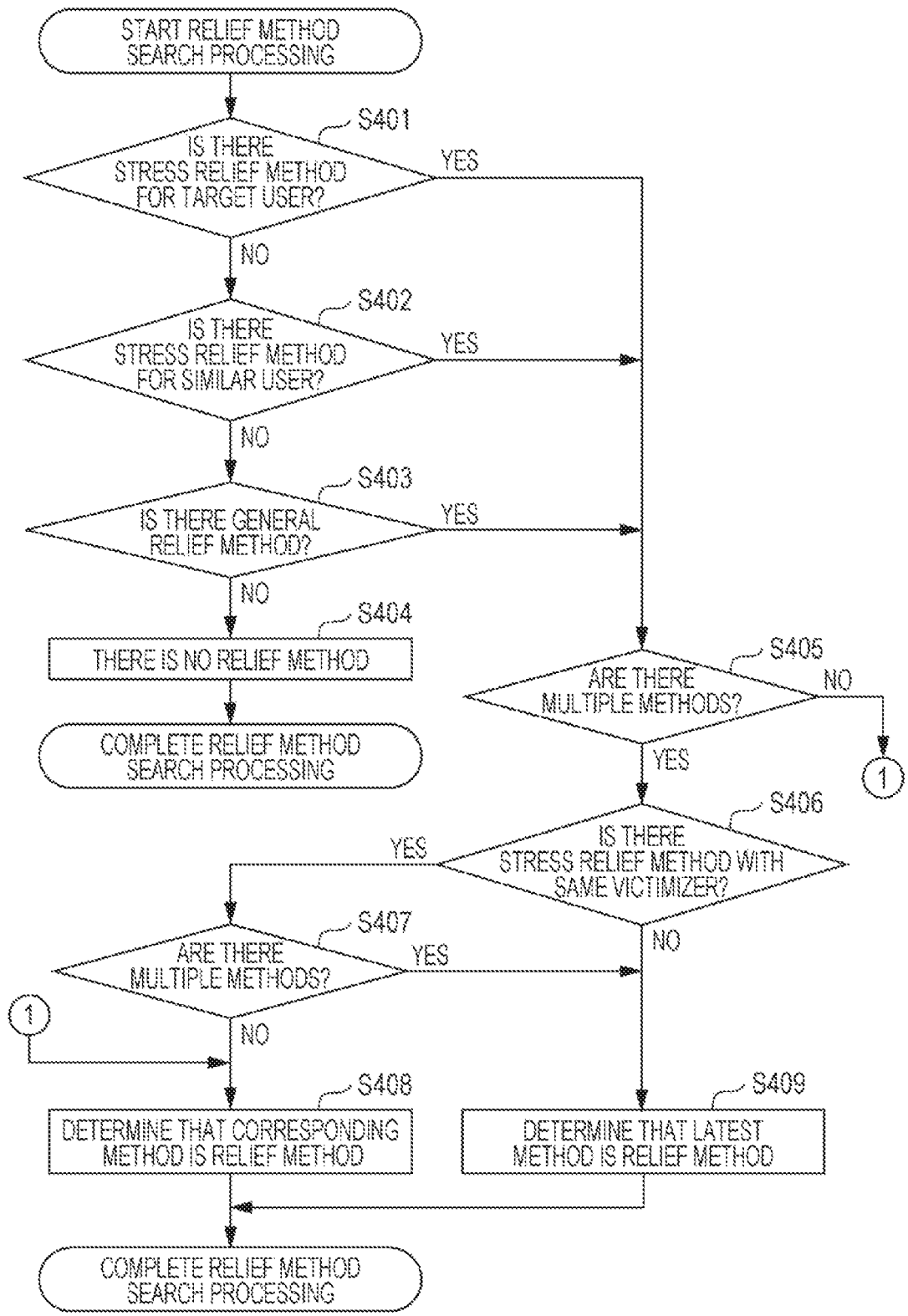
FIG. 14 is a flowchart illustrating the operation of relief method search processing.

Hereinafter, the relief method search processing in S400 illustrated in FIG. 7 will be described in detail. FIG. 14 is a flowchart illustrating the operation of the relief method search processing. As illustrated in FIG. 14, when starting the relief method search processing, the notifier 13 first determines whether or not a stress relief method specific to the target user is present for relieving a type of stress estimated by the cause estimation processing in S300 illustrated in FIG. 7 (S401).

Hereinafter, S401 will be described in detail. FIG. 15 is a table illustrating an example of a specific relief method. As illustrated in FIG. 15, the relief method storage 153 illustrated in FIG. 2 stores a specific relief method table in which the user ID (for instance, "C") of each user, a date (for instance, "2016/7/1") on which stress experienced by the user has been relieved, a type (for instance, "POWER HARASSMENT") of stress experienced by the user, the user ID (for instance, "A") of a victimizer who is the cause of the type of stress experienced by the user, and a stress relief method specific to the user for relieving the type of stress are stored in association with each other. The specific relief method table stores data via the network 9 by an application in the smartphone 22 carried by the user or a personal computer (not illustrated) used by the user.

In S401, the notifier 13 refers to the specific relief method table illustrated in FIG. 15, and determines whether or not a stress relief method (for instance, "DINING OUT" "CONSULTING WITH G") associated with a type (for instance, "POWER HARASSMENT") of stress estimated in S300 is present in the stress relief methods associated with the user ID (for instance, "C") of the target user. Thus, the notifier 13 determines whether or not a stress relief method specific to the target user is present for relieving a type of stress estimated by the cause estimation processing in S300.

In S401, when it is determined that no stress relief method specific to the target user is present (NO in S401), the notifier 13 determines whether or not a stress relief method for a similar user is present for relieving a type of stress estimated by the cause estimation processing in S300 (S402). A similar user is a user who has a profile similar to the profile of the target user. The target user is an example of the first user. The similar user is an example of the second user.

Hereinafter, S402 will be described in detail. FIG. 16 is a table illustrating an example of data stored in the profile storage 154. As illustrated in FIG. 16, the profile storage 154 illustrated in FIG. 2 stores the user ID (for instance, "A") of each of one or more users, and profile data indicating the profile of the user in association with each other beforehand.

The profile of a user includes characteristics of the user: NAME (for instance, "AA"), AGE (for instance, "45"), SEX (for instance, "MALE"), INDUSTRY 1 (for instance, "MANUFACTURING"), INDUSTRY 2 (for instance, "ELECTRIC"), BUSINESS TYPE (for instance, "TECHNICAL"), POST (for instance, "SECTION MANAGER"), and HOBBY (for instance, "GOLF, BASEBALL, DRINKING"). It is to be noted that the profile of a user is not limited to this, and may include, for instance, a final academic background, and a hometown.

In S401, it is assumed that the notifier 13 determines no relief method is present, which is specific to a target user (for instance, the user identified by the user ID "D") associated with a type (for instance, "POWER HARASSMENT") of stress estimated by the cause estimation processing in S300.

In this case, in S402, the notifier 13 first identifies a similar user having a profile similar to the profile of the target user (for instance, the user identified by the user ID "D") based on the profile indicated by the profile data of one or more users, stored in the profile storage 154 illustrated in FIG. 2.

Specifically, from the profile storage 154, the notifier 13 obtains profile data (for instance, NAME "DD", AGE "25", SEX "FEMALE", INDUSTRY 1 "MANUFACTURING", INDUSTRY 2 "ELECTRIC", BUSINESS TYPE "SALES", POST "LOWLY EMPLOYEE", HOBBY "MOVIE WATCHING, TRAVEL") associated with the user ID (for instance, "D") of the target user. Hereinafter profile data associated with the user ID of a target user is called the profile data of a target user.

From the profile data of a plurality of users stored in the profile storage 154, the notifier 13 identifies the profile data of another user, which matches a partial profile (for instance, SEX "FEMALE", INDUSTRY 1 "MANUFACTURING", INDUSTRY 2 "ELECTRIC", POST "LOWLY EMPLOYEE") included in the profile data of a target user.

Here, when a plurality pieces of profile data is identified, from the plurality pieces of profile data, the notifier 13 identifies the profile data of another user, which is closest to other partial profile (for instance, AGE "25", BUSINESS TYPE "SALES") included in the profile data of the target user. The notifier 13 then identifies a similar user as the user identified by the user ID (for instance, "C") associated with the identified profile data.

The notifier 13 then refers to the specific relief method table illustrated in FIG. 15, and determines whether or not a stress relief method (for instance, "DINING OUT" "CONSULTING WITH G") associated with a type (for instance, "POWER HARASSMENT") of stress estimated by the cause estimation processing in S300 illustrated in FIG. 7 is present in the stress relief methods associated with the user ID (for instance, "C") of the identified similar user. Thus, the notifier 13 determines whether or not a stress relief method for a similar user is present for relieving a type of stress estimated by the cause estimation processing in S300.

In S402 illustrated in FIG. 14, when it is determined that no stress relief method for a similar user is present (NO in S402), the notifier 13 determines whether or not a general stress relief method is present for relieving a type of stress estimated by the cause estimation processing in S300 (S403).

Hereinafter, S403 will be described in detail. FIG. 17 is a table illustrating an example of a general relief method table. As illustrated in FIG. 17, the relief method storage 153 illustrated in FIG. 2 stores a general relief method table in which a type (for instance, "POWER HARASSMENT") of stress, a general stress relief method (for instance, "CONSULTING WITH SUPERVISOR OF ANOTHER DEPARTMENT", "CONSULTING WITH COUNSELLOR") for relieving the type of stress, and the date (for instance, "2016/7/1", "2016/7/25") on which the stress relief method is stored are stored in association with each other beforehand.

In S403, the notifier 13 refers to the general relief method table illustrated in FIG. 17, and determines whether or not a stress relief method (for instance, "CONSULTING WITH SUPERVISOR OF ANOTHER DEPARTMENT", "CONSULTING WITH COUNSELLOR") associated with a type (for instance, "POWER HARASSMENT") of stress estimated by the cause estimation processing in S300 is present. Thus, the notifier 13 determines whether or not a general stress relief method for relieving a type of stress estimated by the cause estimation processing in S300 is present.

In S403, when it is determined that a general stress relief method is not present (NO in S403), the notifier 13 determines that no stress relief method for relieving a type of stress estimated by the cause estimation processing in S300 is present (S404), and completes the relief method search processing.

It is assumed that the notifier 13 determines in S401 that only one stress relief method specific to the target user is present (YES in S401, NO in S405). Otherwise it is assumed that the notifier 13 determines in S402 that only one stress relief method for a similar user is present (YES in S402, NO in S405). Otherwise it is assumed that the notifier 13 determines in S403 that only one general stress relief method is present (YES in S403, NO in S405). In these cases, the notifier 13 determines that the only one stress relief method present is the stress relief method for relieving a type of stress estimated by the cause estimation processing in S300 (S408), and completes the relief method search processing.

Otherwise it is assumed that the notifier 13 determines in S401 that multiple stress relief methods specific to the target user are present (YES in S401, YES in S405). Otherwise it is assumed that the notifier 13 determines in S402 that multiple stress relief methods for a similar user are present (YES in S402, YES in S405). Otherwise it is assumed that the notifier 13 determines in S403 that multiple general stress relief methods are present (YES in S403, YES in S405).

In these cases, the notifier 13 determines whether or not out of the multiple stress relief methods, a stress relief method (hereinafter called a stress relief method for the same victimizer) is present for relieving stress caused by the same victimizer as the victimizer estimated by the cause estimation processing in S300 (S406).

For instance, it is assumed that the notifier 13 determines in S403 that multiple general stress relief methods are present (YES in S403, YES in S405), and performs S406. In this case, in the general relief method table illustrated in FIG. 17, a type of stress and a date are associated with a general stress relief method, however, a victimizer is not associated with a general stress relief method. Therefore, the notifier 13 determines in S406 that no stress relief method for the same victimizer is present (NO in S406).

In this case, out of multiple stress relief methods (for instance, two stress relief methods associated with the type "POWER HARASSMENT" in FIG. 17), the notifier 13 determines that the stress relief method (for instance, "CONSULTING WITH COUNSELLOR") associated with the latest date (for instance, "2016/7/25") is the stress relief method for relieving a type of stress estimated by the cause estimation processing in S300 (S409), and completes the relief method search processing.

It is assumed that the notifier 13 determines in S401 that multiple stress relief methods for the user himself/herself are present (YES in S401, YES in S405), and performs S406. Otherwise it is assumed that the notifier 13 determines in S402 that multiple stress relief methods for a similar user are present (YES in S402, YES in S405), and performs S406.

In these cases, in S406, the notifier 13 determines whether or not a stress relief method (for instance, "DINING OUT") associated for the same victimizer as a victimizer (for instance, "A") estimated by the cause estimation processing in S300 is present out of the multiple stress relief methods (for instance, two stress relief methods associated with the type "POWER HARASSMENT") in the specific relief method table illustrated in FIG. 15. Thus, the notifier 13 determines whether or not a stress relief method for the same victimizer is present out of the multiple stress relief methods.

When it is determined in S406 that only one stress relief method for the same victimizer is present (YES in S406, NO in S407), the notifier 13 determines that the only one stress relief method for the same victimizer is the stress relief method for relieving a type of stress estimated by the cause estimation processing in S300 (S408), and completes the relief method search processing.

Thus, it is possible to search for a stress relief method for more appropriately relieving a type of stress estimated by the cause estimation processing in S300, caused by the same victimizer as a victimizer estimated by the cause estimation processing in S300.

It is assumed that the notifier 13 determines in S406 that multiple stress relief methods for the same victimizer are present (YES in S406, YES in S407). In this case, out of multiple stress relief methods for the same victimizer, the notifier 13 determines that the stress relief method for the same victimizer associated with the latest date in the specific relief method table illustrated in FIG. 15 is the stress relief method for relieving a type of stress estimated by the cause estimation processing in S300 (S409). The notifier 13 then completes the relief method search processing.

Thus, it is possible to search for a latest stress relief method for more appropriately relieving a type of stress estimated by the cause estimation processing in S300, caused by the same victimizer as a victimizer estimated by the cause estimation processing in S300.

In this manner, in S500 illustrated in FIG. 7, the notifier 13 notifies the target user of a stress relief method determined in the relief method search processing in S400. For this reason, the user can efficiently relieve the interpersonal stress being experienced by the user by conducting an activity in accordance with the notified stress relief method without performing an unnecessary action.

Also, even when a stress relief method specific to a target user for relieving the type of stress being experienced by the target user is not present, if a stress relief method for a similar user for relieving the type of stress is present, the notifier 13 may determine that the stress relief method for a similar user is the method for relieving the stress being experienced by the target user, and may notify the target user of the stress relief method.

In other words, a stress relief method for users with similar profiles may not be stored in the specific relief method table individually in association with each user ID of the users, but may be stored in the specific relief method table in association with the user ID of either user, thereby making it possible to notify the users with similar profiles of the same stress relief method. Thus, it is possible to avoid redundantly storing a stress relief method for users with similar profiles in the specific relief method table. Consequently, the storage capacity necessary for storing the specific relief method table can be saved.

It is to be noted that in the specific relief method table illustrated in FIG. 15, a flag indicating whether or not a user identified by user ID associated with a stress relief method has relieved the type of stress associated with the stress relief method may be further stored in association with the stress relief method. Thus, a result of whether or not stress has been relieved by conducting an activity in accordance with a stress relief method specific to a user may be stored by the user in the specific relief method table illustrated in FIG. 15 as the flag associated with the stress relief method specific to the user.

In this case, in S409 illustrated in FIG. 14, when stress relief methods for the same victimizer are present, each of which is associated with a flag indicating that stress can be relieved, a stress relief method for the same victimizer associated with the latest date out of the stress relief methods for the same victimizer may be determined to be the stress relief method for relieving a type of stress estimated by the cause estimation processing in S300. It is to be noted that when no stress relief method for the same victimizer is present, which is associated with a flag indicating that stress can be relieved, as described above, a stress relief method for the same victimizer associated with the latest date may be determined to be the stress relief method for relieving a type of stress estimated by the cause estimation processing in S300.

Second Embodiment

Figure 18:
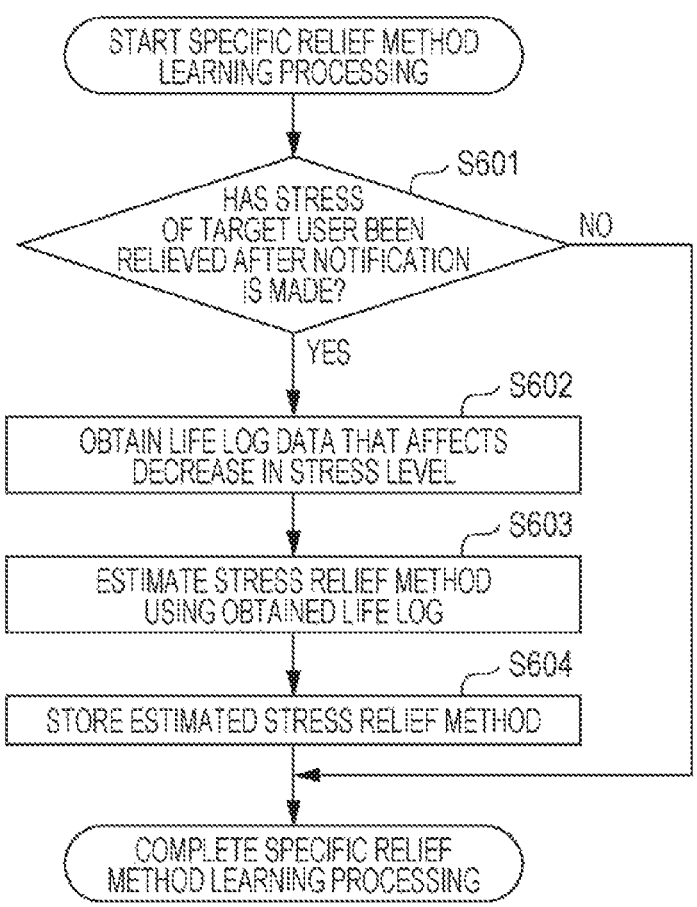
FIG. 18 is a flowchart illustrating the operation of specific relief method learning processing.

In the first embodiment, the specific relief method table illustrated in FIG. 15 stores data via the network 9 by an application in the smartphone 22 carried by the user or a personal computer (not illustrated) used by the user. However, the learner 14 illustrated in FIG. 2 may perform the specific relief method learning processing illustrated in FIG. 18, thereby storing data in the specific relief method table. FIG. 18 is a flowchart illustrating the operation of the specific relief method learning processing.

Specifically, in a predetermined period such as night (for instance, 1:00 a.m.), the learner 14 performs the specific relief method learning processing illustrated in FIG. 18 on each user, as a target user, who is notified of a result of estimation of a type of stress and of a stress relief method by the notifier 13. As illustrated in FIG. 18, when starting the specific relief method learning processing, after the notifier 13 notifies each target user of the notification, the learner 14 determines whether or not the type of stress of which each target user is notified has been relieved (S601).

Hereinafter, S601 will be described in detail. It is to be noted that in the subsequent description, it is assumed that the notifier 13 notifies the user identified by user ID "A" of the notification at 0:00 a.m. on Aug. 2, 2016. Subsequently, the biological data detection processing and the biological data storage processing illustrated in FIG. 3 are performed, and as a consequence, the data illustrated in FIG. 4 is stored in the biological data storage 151. In addition, the life log data detection processing and the life log storage processing illustrated in FIG. 5 are performed, and as a consequence, the data illustrated in FIG. 6 is stored in the life log storage 152. It is assumed that the learner 14 has started the specific relief method learning processing for the user as a target user at 1:00 a.m. on Aug. 3, 2016.

In S601, the learner 14 first causes the generator 11 to generate stress data (hereinafter called post-notification stress data) which indicates a time series variation in the stress level of a target user after the notification by the notifier 13. Specifically, similarly to S100 illustrated in FIG. 7, the learner 14 causes the generator 11 to generate post-notification stress data using the user ID "A" and biological data (for instance, "HEART RATE Ba11", "HEART RATE Ba31") associated with a date and time after 0:00 a.m. on Aug. 2, 2016 in the biological data storage 151 illustrated in FIG. 4.

Next, the learner 14 determines whether or not the stress level included in the post-notification stress data has reduced below a threshold value used in S200 illustrated in FIG. 7. In this manner, the learner 14 determines whether or not the stress level included in the post-notification stress data has reduced below a threshold value, thereby determining whether or not the type of stress of which the target user is notified has been relieved after the notifier 13 notifies the target user of the notification.

In S601, when it is determined that the type of stress of which the target user is notified has not been relieved (NO in S601), the learner 14 completes the specific relief method learning processing. Subsequently, the learner 14 performs the specific relief method learning processing on another user who is notified of the notification by the notifier 13.

On the other hand, in S601, when it is determined that the type of stress of which the target user is notified has been relieved (YES in S601), the learner 14 obtains life log data corresponding to the detection time of biological data that relates a decrease in the stress level of the target user (S602).

Specifically, in S602, from the biological data storage 151 illustrated in FIG. 4, the learner 14 obtains a date (for instance, "2016/8/2") and a time (for instance, "10:30") associated with biological data (for instance, "HEART RATE Ba11") used for calculation of a stress level which is determined to be lower than a threshold value in S601. Thus, the learner 14 recognizes the time point (for instance, "2016/8/2 10:30") indicated by the obtained date and time as the detection time of biological data that relates a decrease in the stress level, The learner 14 then refers to the data (FIG. 6) stored in the life log storage 152, and obtains life log data (for instance, "VOICE DATA A1") associated with date and hours (for instance, "2016/8/2", "10:00-12:00") including the recognized detection time (for instance, "2016/8/2 10:30") of biological data out of life log data (for instance, "VOICE DATA A1", "VOICE DATA A3") associated with the user ID (for instance, "A") of the target user. Thus, the learner 14 obtains life log data corresponding to the detection time of biological data that relates a decrease in the stress level. In other words, the learner 14 recognizes the activity of the target user indicated by the obtained life log data as an activity that affects a decrease in the stress level.

The learner 14 estimates a method for relieving the stress being experienced by the target user, using the life log data obtained in S602 (S603), The learner 14 then stores the method estimated in S603 as a stress relief method corresponding to the type of stress being experienced by the target user in the specific relief method table illustrated in FIG. 15 (S604).

Hereinafter, S603 and S604 will be described in detail. For instance, in S603, the learner 14 performs publicly known voiceprint recognition processing, thereby determining whether or not the user voice data stored in the storage 15 has user voice data with a voiceprint matching a voiceprint included in voice data included in the life log data obtained in S602.

When it is determined that user voice data with a matching voiceprint is present, the learner 14 obtains, from the storage 15, a user ID which is different from the user ID of the target user, out of user IDs associated with the user voice data. Thus, the learner 14 estimates that the user identified by the obtained user ID is the user to be contacted for relieving stress.

On the other hand, when it is determined that user voice data with a matching voiceprint is not present, or the different user ID is not obtainable, the learner 14 does not estimate a user to be contacted for relieving stress.

Also, the storage 15 stores an activity determination table in which an activity for relieving stress (for instance, "CONSULTATION", "DINING OUT", "DRINKING"), and terms which are likely to be used in a conversation at the time of the activity are associated with each other beforehand.

Similarly to S302 illustrated in FIG. 8, the learner 14 performs publicly known voice recognition processing, and thereby converts the voice data included in the life log data obtained in S602 into text data. From the activity determination table, the learner 14 obtains an activity associated with a term matching one of the terms included in the text data. The learner 14 then estimates that an activity obtained most frequently is the activity for relieving the stress being experienced by the user.

When the learner 14 estimates a user to be contacted for relieving stress, the learner 14 estimates that contacting with the user to be contacted and conducting the above-mentioned estimated activity is a method for relieving stress. Also, when the learner 14 does not estimate a user to be contacted for relieving stress, the learner 14 estimates that conducting the above-mentioned estimated activity by the target user himself/herself is a method for relieving stress. It is to be noted that S603 may be implemented by another method without being limited to this.

In S604, the learner 14 stores the user ID of the target user, the date when the specific relief method learning processing was performed, a type of stress and a victimizer of which the target user is notified by the notifier 13, and the method for relieving stress estimated in S603 in the specific relief method table illustrated in FIG. 15 in association with each other.

In this manner, according to the configuration of the second embodiment, a stress relief method specific to a user can be efficiently stored in the specific relief method table without extra effort of the user.

It is to be noted that the first and second embodiments are merely illustrative of embodiments according to the present disclosure, and it is not intended to limit the present disclosure to the first and second embodiments. For instance, modifications illustrated below may be provided.

First Modification

The specific relief method table illustrated in FIG. 15 in the first embodiment may further store, in association with a stress relief method, product information which indicates usable products at a time when an activity is conducted in accordance with the stress relief method. For instance, in association with a stress relief method "DINING OUT" in the first row of the specific relief method table illustrated in FIG. 15, product information which indicates products such as a wallet usable at the time of dining out or a meal ticket may be stored.

Accordingly, in S500 illustrated in FIG. 7, the notifier 13 may further notify the target user of product information associated, in the specific relief method table, with a stress relief method to be notified to the target user.

In this case, when an activity is conducted in accordance with a stress relief method of which the target user is notified, it is possible to increase the opportunity of utilizing the products indicated by product information of which the target user is notified.

Second Modification

In the first and second embodiments, description is given under the assumption that the life log data includes only voice data which indicates the voice when a user conducts an activity. However, without being limited to this, the life log data may include image data which indicates a situation when a user conducts an activity.

In this case, the storage 15 may store the user ID of each user, and image data (hereinafter called user image data) indicating the face of each user in association with each other beforehand. In S304, S306 and S308 illustrated in FIG. 8, when the estimator 12 estimates a victimizer who is the cause of stress, an image indicating the face of a person may be recognized from image data included in the life log data by performing publicly known image recognition processing. The estimator 12 may obtain, from the storage 15, a user ID which is different from the user ID of the target user, out of user IDs associated with user image data which has a characteristic substantially matched with that of the recognized face image. The estimator 12 may estimate that the user identified by the obtained user ID is a victimizer who is the cause of stress. In a similar manner to this, in S603 illustrated in FIG. 18, the learner 14 may estimate a user to be contacted for relieving stress using image data included in the life log data.

Third Modification

The life log data in the second embodiment may include position information which indicates the existing position of the smartphone 22 detected by Global Positioning System (GPS) sensor provided in the smartphone 22. Similarly, life log data transmitted from the monitoring device 3 may include identification information of a room in which the monitoring device 3 is installed.

In this case, in S603 illustrated in FIG. 18, the learner 14 may include position information or identification information of a room included in the life log data used for estimation of a stress relief method in a stress relief method estimated in S603 illustrated in FIG. 18 as information indicating a location suitable for conducting an activity to relieve stress.

Fourth Modification

The life log data in the second embodiment may include environmental information which indicates an environment of the location where the smartphone 22 is present, such as a temperature or a humidity detected by a temperature sensor or a humidity sensor provided in the smartphone 22. Similarly, as the monitoring device 3, a temperature sensor or a moisture sensor may be provided in a room such as a conference room or a classroom. The life log data may include environmental information indicating an environment in the above-mentioned rooms, such as a temperature or a humidity detected by the temperature sensor or the humidity sensor.

In this case, in S603 illustrated in FIG. 18, the learner 14 may include environmental information in a stress relief method estimated in S603 illustrated in FIG. 18 as information indicating an environment suitable for conducting an activity to relieve stress, the environmental information being included in the life log data used for estimation of a stress relief method.

Fifth Modification

The stress management system 100 may not be provided with the monitoring device 3, and the biological data detector 4 and the life log detector 5 illustrated in FIG. 2 may be formed of only the smartphone 22 including a biological sensor.

Sixth Modification

A card reader having the same function as that of the card reader 33 illustrated in FIG. 1 may be built in the individual identification card 23 illustrated in FIG. 1. In this case, when another user having the individual identification card 23 approaches a user having the individual identification card, the card reader built in the individual identification card may obtain profile data stored in a memory chip within the individual identification card 23 of the another user. The card reader may transmit predetermined information (for instance, a user ID) included in the obtained profile data to the server 1.

For instance, it is assumed that a user having an individual identification card in which the card reader is built in is experiencing interpersonal stress. In this case, when a victimizer of the interpersonal stress, having the individual identification card 23 approaches the user, even when the user is unaware of the approach of the victimizer, the user ID included in the profile data stored in a memory chip within the individual identification card of the user, and the user ID of the victimizer obtained from the individual identification card of the victimizer can be transmitted to the server 1. Thus, the server 1 can recognize that the user and the victimizer are approaching each other.

Thus, when the server 1 estimates that the user is experiencing interpersonal stress in S300 illustrated in FIG. 7, a message saying that the victimizer is approaching may be transmitted to the user similarly to S500 illustrated in FIG. 7. In this manner, the user may be informed of approach of the victimizer.

Also, the life log data may include image data which indicates a situation when the user conducts an activity.

Seventh Modification

The storage area owned by the storage 15 illustrated in FIG. 2 is not used as the schedule storage 155, and S307 and S308 illustrated in FIG. 8 may be omitted.

Eighth Modification

The storage area owned by the storage 15 illustrated in FIG. 2 is not used as the profile storage 154, and S402 illustrated in FIG. 14 may be omitted.

Ninth Modification

The storage area owned by the storage 15 illustrated in FIG. 2 is not used as the relief method storage 153, and S400 illustrated in FIG. 7 may be omitted. Accordingly, in S500 illustrated in FIG. 7, the notifier 13 may notify the target user of only a result of the estimation in S300.

10th Modification

In S304, S306, S308 illustrated in FIG. 8, the estimator 12 may not estimate a type of stress and a victimizer who is the cause of stress.

The present disclosure is useful for reducing interpersonal stress experienced by the members of an organization such as a company or a school.

What is claimed is:

1. A stress management system, comprising:
a first sensor that detects biological data of a user;
a second sensor that detects life log data including voice data relating to an activity of the user;
a memory that stores instructions;
a processor, when executing the instructions stored in the memory, that performs operations including:
generating stress data using the biological data, the stress data indicating a time series variation in a stress level of the user;
determining, when the stress level included in the stress data exceeds a threshold value, whether or not stress experienced by the user is interpersonal stress that is caused by contact with other people, using the life log data; and
notifying the user that the stress is interpersonal stress, when the stress is determined as interpersonal stress,
wherein the determining of whether or not the stress experienced by the user is interpersonal stress comprising:
determining whether or not the voice data of the life log data includes a term included in a predetermined interpersonal stress table including terms indicating interpersonal stress, the term being only a word or a sequence of words; and
determining that the stress experienced by the user is interpersonal stress when the voice data of the life log data includes the term included in the predetermined interpersonal stress table.

2. The stress management system according to claim 1, wherein when the stress experienced by the user is determined to be interpersonal stress, the processor further determines a type of interpersonal stress and a victimizer who is a cause of interpersonal stress, using the life log data.

3. The stress management system according to claim 2, further comprising:
a first storage that stores, for each user, a stress relief table, in which each type of interpersonal stress and a stress relief method for relieving a corresponding type of interpersonal stress are associated with each other; and
a second storage that stores a user profile table in which each user is associated with a profile of corresponding user, wherein
the processor further performs operations including:
referring to the stress relief table of a first user,
when a stress relief method that is associated with the determined type of interpersonal stress is not present in the stress relief table of the first user,
referring to the user profile table and identifying a second user who has a profile similar to a profile of the first user,
referring to the stress relief table of the second user, and
notifying the first user of a stress relief method that is associated with the determined type of interpersonal stress in the stress relief table of the second user.

4. The stress management system according to claim 3, wherein the processor further performs operations including:
  after the processor notifies the first user of the stress relief method, when a stress level included in the stress data of the first user falls below the threshold value, determining a stress relief method that has relieved interpersonal stress, using the life log data of the first user, and storing the determined stress relief method in the stress relief table of the first user in association with the determined type of interpersonal stress for the first user.

5. The stress management system according to claim 2, further comprising
  a storage that stores schedule data indicating an activity schedule of the user, wherein
  the processor determines whether or not stress experienced by the user is interpersonal stress that is caused by contact with other people, using the schedule data.

6. The stress management system according to claim 1, wherein the life log data includes image data in which the user is captured.

7. The stress management system according to claim 6, wherein the processor further performs operations including:
  performing an image recognition process on the image data of the life log data;
  identifying a person other than the user in the image data based on a result of the image recognition process; and
  determining that the identified person as a victimizer who causes interpersonal stress of the user.

8. The stress management system according to claim 1, wherein the voice data of the life log data includes a conversation of the user.

9. The stress management system according to claim 1, further comprising
  a first storage that stores a stress relief table in which each type of interpersonal stress and a stress relief method for relieving a corresponding type of interpersonal stress are associated with each other, wherein
  the processor further performs operations including:
  determining, when the stress is determined as interpersonal stress, a type of interpersonal stress, and
  referring to the stress relief table, and notifying the user of a stress relief method associated with the determined type of interpersonal stress in the stress relief table.

10. The stress management system according to claim 9, wherein
  in the stress relief table, each stress relief method is further associated with product information which indicates usable products when an activity is performed in accordance with the stress relief method, and
  the processor refers to the stress relief table, and notifies the user of the product information associated with the stress relief method which is associated with the determined type of interpersonal stress.

11. The stress management system according to claim 1, further comprising a terminal that includes both the first sensor and the second sensor.

12. The stress management system according to claim 1, wherein the processor further performs operations including:
  determining whether or not the voice data of the life log data includes a term included in a predetermined non-interpersonal stress table including terms indicating non-interpersonal stress; and
  determining that the stress experienced by the user is not interpersonal stress when the voice data of the life log data includes the term included in the predetermined non-interpersonal stress table.

13. The stress management system according to claim 12, wherein
  the determining of whether or not the voice data of the life log data includes a term included in a predetermined non-interpersonal stress table is performed after it is determined that the voice data of the life log data does not include the term included in the predetermined interpersonal stress table, and
  the processor further performs operations including:
  determining that the stress experienced by the user is caused by an unknown reason, when the voice data of the life log data does not include the term included in the predetermined non-interpersonal stress table.

14. The stress management system according to claim 1, wherein
  the predetermined interpersonal stress table includes at least a first interpersonal stress table including terms indicating a first type of interpersonal stress and a second interpersonal stress table including terms indicating a second type of interpersonal stress,
  determining of whether or not the voice data of the life log data includes a term included in the predetermined interpersonal stress table comprising:
    determining whether or not the voice data of the life log data includes a term included in the first interpersonal stress table;
    when it is determined that the voice data of the life log data includes the term included in the first interpersonal stress table, determining that the stress experienced by the user is the first type of interpersonal stress;
    when it is determined that the voice data of the life log data does not include the term included in the first interpersonal stress table, determining whether or not the voice data of the life log data includes the term included in the second interpersonal stress table; and
    when it is determined that the voice data of the life log data includes the term included in the second interpersonal stress table, determining that the stress experienced by the user is the second type of interpersonal stress.

15. The stress management system according to claim 14, wherein
  the first type of interpersonal stress is one of power harassment and sexual harassment, and
  the second type of interpersonal stress is the other one of power harassment and sexual harassment.

16. The stress management system according to claim 1, further comprising
  a storage that stores schedule data, including a scheduled activity to be performed by the user associated with a scheduled time at which the scheduled activity is to be performed by the user, and technical terms associated with the scheduled activity included in the schedule data, wherein
  the processor further performs operations including:
  acquiring, from the storage, the schedule data which includes the scheduled time including a time when the life log data is detected by the second sensor;
  determining whether or not the voice data of the life log data includes one of the technical terms associated with the scheduled activity included in the acquired schedule data; and
  determining that the stress experienced by the user is interpersonal stress, when it is determined that the voice data of the life log data includes one of the technical terms associated with the scheduled activity included in the acquired schedule data.

17. A stress management method, comprising:
detecting biological data of a user;
detecting life log data including voice data relating to an activity of the user;
generating stress data using the biological data, the stress data indicating a time series variation in a stress level of the user;
determining, when the stress level included in the stress data exceeds a threshold value, whether or not stress experienced by the user is interpersonal stress that is caused by contact with other people, using the life log data; and
notifying the user that the stress is interpersonal stress, when the stress is determined as interpersonal stress,
wherein the determining of whether or not the stress experienced by the user is interpersonal stress comprising:
determining whether or not the voice data of the life log data includes a term included in a predetermined interpersonal stress table including terms indicating interpersonal stress, the term being only a word or a sequence of words; and
determining that the stress experienced by the user is interpersonal stress when the voice data of the life log data includes the term included in the predetermined interpersonal stress table.

18. A stress management system, comprising:
a first sensor that detects biological data of a user;
a second sensor that detects life log data including voice data relating to an activity of the user;
a storage that stores a stress relief table in which each type of interpersonal stress and a stress relief method for relieving a corresponding type of interpersonal stress are associated with each other;
a memory that stores instructions; and
a processor, when executing the instructions stored in the memory, that performs operations including:
generating stress data using the biological data, the stress data indicating a time series variation in a stress level of the user;
determining, when the stress level included in the stress data exceeds a threshold value, whether or not stress experienced by the user is interpersonal stress that is caused by contact with other people, using the life log data;
notifying the user that the stress is interpersonal stress, when the stress is determined as interpersonal stress,
determining, when the stress is determined as interpersonal stress, a type of interpersonal stress;
referring to the stress relief table; and
notifying the user of a stress relief method associated with the determined type of interpersonal stress in the stress relief table.

19. A stress management method, comprising:
detecting biological data of a user;
detecting life log data including voice data relating to an activity of the user;
generating stress data using the biological data, the stress data indicating a time series variation in a stress level of the user;
determining, when the stress level included in the stress data exceeds a threshold value, whether or not stress experienced by the user is interpersonal stress that is caused by contact with other people, using the life log data;
notifying the user that the stress is interpersonal stress, when the stress is determined as interpersonal stress;
determining a type of interpersonal stress, when the stress is determined as interpersonal stress;
referring to a stress relief table in which each type of interpersonal stress and a stress relief method for relieving a corresponding type of interpersonal stress are associated with each other; and
notifying the user of a stress relief method associated with the determined type of interpersonal stress in the stress relief table.

* * * * *